United States Patent
Inoue et al.

(10) Patent No.: US 6,597,947 B1
(45) Date of Patent: Jul. 22, 2003

(54) IONTOPHORESIS DEVICE

(75) Inventors: Kazutaka Inoue, Tsukuba (JP);
Hirotoshi Adachi, Tsukuba (JP);
Hiroyuki Maeda, Tsukuba (JP);
Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/958,599

(22) PCT Filed: Apr. 6, 2000

(86) PCT No.: PCT/JP00/02236
§ 371 (c)(1), (2), (4) Date: Oct. 12, 2001

(87) PCT Pub. No.: WO00/61220
PCT Pub. Date: Oct. 19, 2000

(30) Foreign Application Priority Data

Apr. 13, 1999 (JP) ............................................ 11-105385

(51) Int. Cl.$^7$ .................................................. A61N 1/30
(52) U.S. Cl. ........................................ 604/20; 604/890.1
(58) Field of Search ................................. 604/20, 890.1

(56) References Cited

U.S. PATENT DOCUMENTS 5,533,971 A * 7/1996 Phipps .......................... 604/20
6,006,130 A * 12/1999 Higo et al. ..................... 604/20

FOREIGN PATENT DOCUMENTS

| JP | WO 96/17649 | * 6/1996 |
| JP | 0813887 A2 | * 12/1997 |
| WO | WO 95/27528 | * 10/1995 |

* cited by examiner

Primary Examiner—Michael J. Hayes
Assistant Examiner—Kathryn L. Thompson
(74) Attorney, Agent, or Firm—Townsend & Banta

(57) ABSTRACT

The present invention provides an iontophoresis device allowing effective and continuous absorption for a long period. The iontophoresis device comprises the first electrode structure (100a) and the second electrode structure (110a) each having a hydrophilic conductive layer (102a, 112a) containing active ingredient and an electrode member (101a, 111a), and a power supply (120a) having polarity inverting means for switching over a current direction between the two electrode structures, wherein at least one of the first and the second electrode structures contains chloride ions and before administration, a chloride-ion content (P mg) is within a range satisfying the following equation:

$$1.0 \times (I \times T \times 0.022) \leq P$$

wherein T represents a polarity inverting time (min) until polarity is inverted after energization in a certain direction and I represents an average current (mA).

20 Claims, 4 Drawing Sheets

IONTOPHORESIS DEVICE

TECHNICAL FIELD

The present invention relates to a polarity-inverting type iontophoresis device capable of controlling transdermal or transmucosal drug administration for a long time. In particular, the present invention relates to an iontophoresis device which can effectively maintain safe and stable absorptivity for a long time utilizing electric driving force and which can be produced with a low cost.

BACKGROUND ART

Iontophoresis is a transdermal-absorption promotion system using electricity as external stimulation. It is based on a mechanism that across an electric field generated between an anode and a cathode mainly by energization, molecules with a positive charge move from the anode to the cathode while those with a negative charge move from the cathode to the anode, to generate force, which promotes penetration of a drug molecule through the skin barrier (See, Journal of Controlled Release, Vol. 18, 1992, pp. 213–220; Advanced Drug Delivery Review, Vol. 9, 1992, p.119; Pharmaceutical Research Vol. 3, 1986, pp. 318–326).

Iontophoresis generally involves a power supply, a drug reservoir electrode and an electrolyte reservoir electrode. An electrode which may be used in this system may be an active electrode such as a silver or silver chloride electrode or an inactive electrode such as a platinum or titanium electrode. In case of an inactive electrode, hydrogen ions and oxygen gas are generated on an anode side and hydroxyl ions or hydrogen gas are generated during energization on a cathode side. It is well known that hydrogen ions and hydroxyl ions generated by the inactive electrode may induce skin irritation or reduce of a drug delivery rate.

Anode side: $2H_2O \rightarrow 4H^+ + O_2 + 4e^-$

Cathode side: $2H_2O + 2e^- \rightarrow 2OH^- + H_2$

On the other hand, in an active electrode, a redox reaction occurs at a lower voltage than that in electrolysis of water. Typical electrode materials include silver and silver chloride. Generally, an anode is made of a silver electrode and an electrolyte reservoir contains a counter material, e.g., chloride ions, required for a redox reaction with the electrode. Thus, metal ions (e.g., silver ions) eluted from the anode electrode react with chloride ions in the reservoir to form an insoluble precipitate (e.g., silver chloride). It can substantially inhibit transfer of the metal ions to the skin so that an active electrode is safer to the skin than an inactive electrode.

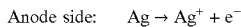
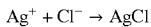

Anode side: $Ag \rightarrow Ag^+ + e^-$ $Ag^+ + Cl^- \rightarrow AgCl$

Cathode side: $AgCl + e^- \rightarrow Ag + Cl^-$

Use of an active electrode has, however, encountered problems of competition between a cationic drug and counter ion species to chloride ions in an anode side and reduction in absorptivity due to competition between an anionic drug and chloride ions eluted from the electrode in a cathode side. An active electrode itself may be oxidized or reduced. It is, therefore, difficult to maintain performance as an active electrode for a long-term use.

Thus, devices and methods have been recently developed for solving the problem of competitive ions in the above electrode. In particular, there has been improvement in terms of competitive ions eluted from an electrode, which represents a problem in use of an active electrode. As a method for inhibiting such metal-ion transfer in an active electrode, National Publication of the International Patent Application Nos. 3-504813 and 3-504343 have disclosed a device where a material causing an electrode reaction at a lower voltage than that in hydrolysis of water is used as a current distributing member and a charge-selecting material layer is placed between an electrode and a drug reservoir or between the body surface and an electrode. The charge-selecting material contains counter ions reacting with the electrode. National Publication of the International Patent Application No. 5-506158 has disclosed a device comprising a donor electrode, an electrolyte reservoir, a selective permeable membrane and a drug reservoir, where the electrolyte reservoir contains counter ions reacting with the electrode. In these techniques, it has been indicated that counter ions to the counter ions reacting with the electrode have the same polarity as a drug, leading to a reduction in the drug delivery rate and that a chloride bound to a polymer (e.g., quaternary ammonium chloride) may be used to avoid the problem. Such modification, however, mainly aims at effective drug delivery and there have remained problems in terms of practicability and versatility due to its complex structure. There have been disclosed no means for maintaining electrode performance for a long-term use.

Electrode materials which may be used in an active electrode such as silver and silver chloride are generally expensive. Thus, in practical production, incorporating these metal materials (for example, a silver foil) in a device is undesirable in terms of productivity and a production cost. Furthermore, there have been significant problems for developing an iontophoresis device for a long-term use, i.e., problems in terms of maintaining electrode performance for a long time such as life expiration due to electrode deterioration in an active electrode such as a silver or silver chloride electrode, i.e., insulation in an electrode due to precipitation of non-conductive silver chloride on the electrode surface caused by long-term energization in an anode side and life expiration as an active electrode due to elution of chlorine from silver chloride during energization in a cathode side.

On the other hand, there have been developed electrodes improved for long-term use. Japanese Patent Laid-Open Publication No. 9-276416 has disclosed an electrode comprising a main electrode consisting of an active electrode and a regeneration electrode as an inactive electrode. Japanese Patent Laid-Open Publication No. 4-312471 has disclosed a device which can be used for a long time using a removable electrolyte reservoir in a housing comprising an inactive electrode. This publication has, however, disclosed regeneration or reuse of an electrode itself in the device using an active electrode and has not consider effects on drug absorptivity induced by competing ions generated during energization and an electrolyte added so that absorption cannot be strictly controlled.

Furthermore, there have been developed devices using a polarity inverting apparatus. For inhibiting generation of harmful hydrogen or hydroxyl ions in an inactive electrode, adjustment of pH by switching polarity is disclosed in Japanese Patent Publication No.60-34396 in which a ratio of a positive current energy amount to a negative current energy amount is within a range of about 2:1 to 7:1 and in EP 0776676 using 0.0027 Hz to 10 Hz. Japanese Patent Laid-Open Publication No. 4-224770 has disclosed that a sign of voltage applied between electrodes is inverted to adjust pH. In such a device, an inactive electrode which is not deteriorated is used and polarity is inverted during energization to inhibit pH variation for improvement in skin irritation. The technique does not improve the problem of generation of gases such as oxygen and hydrogen so that when it is used for a long period, a gas may fill the device and a special structure such as a vent hole is necessary. There has not been thus solved the problem of difficulty in producing an electrode comprising such an element.

In addition, U.S. Pat. No. 4,406,658 has disclosed that a device by which polarity of an electrode can be inverted comprises means for inverting polarity of an electrode to conduct iontophoresis in both electrodes with one application. National Publication of the International Patent Application No. 9-503136 has described that polarity may be inverted to reduce irritation during energization. In the above prior art, no device has been described, which provides safe and stable absorption for a long period, rather than a polarity inverting device for long-term drug delivery.

On the other hands, many diseases require sustained drug delivery for a long period. A patient with such a disease has been substantially treated by invasive procedures such as infusion. Treatment with infusion, however, not only requires hospitalization but also more imposes a burden on a patient. For overcoming such disadvantages, some formulations such as a sustained formulation and an implant have been investigated, but there is limitation of such a formulation in strictly controlling a blood level. Furthermore, when a serious side reaction occurs, drug administration cannot be discontinued. Iontophoresis has been also paid attention as a new drug delivery system in place of an injection as an administration system for a drug requiring strict administration control. If an iontophoresis formulation by which absorption to the same level as that in an injection may be achieved and which allows a patient to administer a drug by him/herself is developed, home treatment may be realized. Precise control of an energization time may allow a given absorption pattern to be achieved. In particular, it may lead to more effective drug treatment for a drug requiring administration control.

DISCLOSURE OF THE INVENTION

An object of the present invention is to provide an iontophoresis device whereby effective and continuous absorption may be maintained for a long period. Another object of the present invention is to provide a long-term type iontophoresis device with higher safety, versatility and practicability which can maintain electrificity and absorpability without reducing a drug delivery rate which provide high bioavailability of a drug the present invention may be generally applicable to the skin, but also applicable to the mucosa.

The inventors have intensely attempted for achieving the above objects and have finally found that two electrode structures (first and second electrode structures) comprising an electrode member consisting of a mixture containing silver and silver chloride contain given amounts of chloride ions and of an active ingredient and energization is conducted using a power supply equipped with polarity inverting means to achieve safe, effective and continuous absorption for a long period. After further investigation, we have also found that irrespective to polarity of a drug, in this device, a chloride-ion content may be selected depending on a time of polarity-inverting for inhibiting transfer of competing ions, to allow the drug to be transdermally administered with a higher bioavailability and good reproducibility. The present invention discloses a chloride-ion content in an electrode structure comprising an active electrode, a substance for supplying chloride ions and an optimal device, in order to allow safe energization for a long period time without causing a reduction of absorption efficiency by means of an energization method using polarity inverting means. It may provide a safe and inexpensive polarity-inverting type iontophoresis device which can strictly control drug administration for a long period.

In particular, for polarity at initial energization, when the first and the second electrode structures are an anode side and an cathode side, respectively, chloride ions in the first electrode structure react with silver ions in the electrode in the anode side, while in the cathode side, silver chloride in the electrode member is oxidized, resulting in elution of chloride ions into the second electrode structure.

Initial electrode reaction in the first electrode structure:
$Ag^+ + Cl^- \rightarrow AgCl$ Initial electrode reaction in the second electrode structure:
$AgCl + e^- \rightarrow Ag + Cl^-$ After polarity inversion, in the anode side, silver chloride precipitated on the electrode surface in the initial electrode reaction is oxidized and chloride ions are eluted into the first electrode structure. In the cathode side, chloride ions eluted into the second electrode structure in the initial electrode reaction react with silver ions in the electrode member.

Initial electrode reaction in the first electrode structure:
$AgCl + e^- \rightarrow Ag + Cl^-$ Initial electrode reaction in the second electrode structure:
$Ag^+ + Cl^- \rightarrow AgCl$ These electrode reactions may be utilized to optimize the chloride-ion content in the first electrode structure and a polarity inverting time and thus energization can be maintained for a long period. On the other hand, when polarity is inverted after energization to a certain direction, chloride ions in the anode side which subsequently react with the electrode are limited to those which have been eluted from the electrode. Thus, the amount of chloride ions which can react with the electrode is limited. A polarity inverting time must be, therefore, strictly controlled. When an irreversible reaction occurs between anions extracted from the skin in the anode side and silver ions eluted from the electrode, the content of silver in the electrode plays an important role in long-term energization. It means that the contents of silver and silver chloride in the electrode must be adjusted, depending on an energization time and a polarity inverting time.

A preferred embodiment for avoiding these problems is, therefore, a device comprising two electrode structures containing a given amount of chloride ions and at least one active ingredient; an active electrode in each electrode structure, which is made of a mixture containing at least silver and silver chloride; and a power supply equipped with polarity inverting means which is electrically connected to an electrode member in each electrode structure for altering a current direction between two electrode structures. In this type of device, even when an irreversible reaction occurs between anions extracted from the skin and silver ions in the electrode in the anode side or a small deviation occurs in a polarity inverting time, there are no effects during a long-term energization because there are, as silver chloride, chloride ions more than those reacted corresponding to a polarity inverting time in any electrode member and each electrode structure contains chloride ions.

Specifically, an iontophoresis device according to the present invention comprises the first and the second electrode structures comprising a hydrophilic conductive layer containing at least one active ingredient and an electrode member made of an active electrode material, respectively; and a power supply equipped with polarity inverting means which is electrically connected to the electrode members in the first and the second electrode structures between them for altering a current direction between the two electrode structures, wherein at least one of the first and the second electrode structures contains chloride ions and before administration, a chloride-ion content (P mg) is within a range satisfying equation (1):

$$1.0 \times (I \times T \times 0.022) \leq P \quad \ldots (1)$$

wherein T represents a polarity inverting time (min) until polarity is inverted after energization in a certain direction and I represents an average current (mA).

The active ingredient is neutral or cationic and polarity inversion is periodically repeated by the power supply.

Alternatively, an iontophoresis device according to the present invention comprises the first and the second electrode structures comprising a hydrophilic conductive layer containing at least one active ingredient and an electrode member made of an active electrode material, respectively; and a power supply equipped with polarity inverting means which is electrically connected to the electrode members in the first and the second electrode structures between them for altering a current direction between two electrode structures, wherein at least one of the first and the second electrode structures contains chloride ions and before administration, a chloride-ion content (P mg) is within a range satisfying equation (2):

$$1.0 \times (I \times T \times 0.022) \leq P \leq 100 \times (I \times T \times 0.022) \quad \ldots (2)$$

wherein T represents a polarity inverting time (min) until polarity is inverted after energization in a certain direction and I represents an average current (mA).

The active ingredient is anionic and polarity inversion is periodically repeated by the power supply.

The power supply comprises timer means for controlling a polarity inverting time. The above chloride ions are contained in the above hydrophilic conductive layer or an additional hydrophilic conductive layer placed between the electrode member and the hydrophilic conductive layer.

The first and the second electrode structures may have the same composition comprising a given amount of chloride ions and at least one active ingredient.

The electrode member is formed by printing a conductive ink containing at least silver and silver chloride. A composition ratio or mixing ratio of silver and silver chloride in the electrode member is preferably 1:9 to 9:1. The electrode member may further contain a halogenated compound.

The above chloride ions may be supplied from hydrochloric acid. Alternatively, the chloride ions may be supplied from at least hydrochloride of an active ingredient or from at least a resin or polymer containing quaternary ammonium chloride. The resin may be selected from the group consisting of ethyl acrylate-methyl methacrylate-ethyl methacrylate trimethylammonium chloride copolymers and cholestyramine.

The electrode structures contain an organic amine as a pH adjusting material. A pH adjusting material is, for example, at least one of meglumine, trometamol, triethanolamine and aminoacrylate. The power supply may comprise means for shorting a circuit in polarity inversion and/or means for providing a non-energization time for a given period. Polarity inversion by the power supply is conducted at least once, where a time for one polarity inversion is preferably 1 min to 2 hours. Current applied by the power supply is at least one of direct current, pulse direct current and pulse depolarized direct current.

The electrode structures comprise an insulating support in which a pit, which accommodates the electrode member and the hydrophilic conductive layer and whose surface may be covered by a semipermeable membrane, a selective permeation membrane, a control membrane or a hydrophilic porous membrane.

BEST MODE FOR CARRYING OUT THE INVENTION

Figure 1:
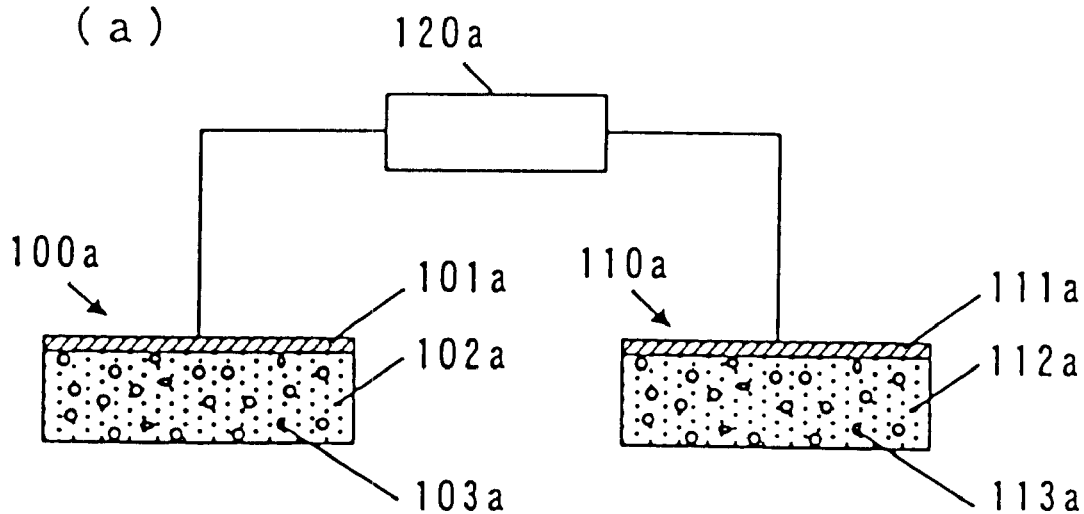
FIGS. 1 (*a*) and (*b*) show a configuration example of an iontophoresis device according to the present invention.
Figure 1:
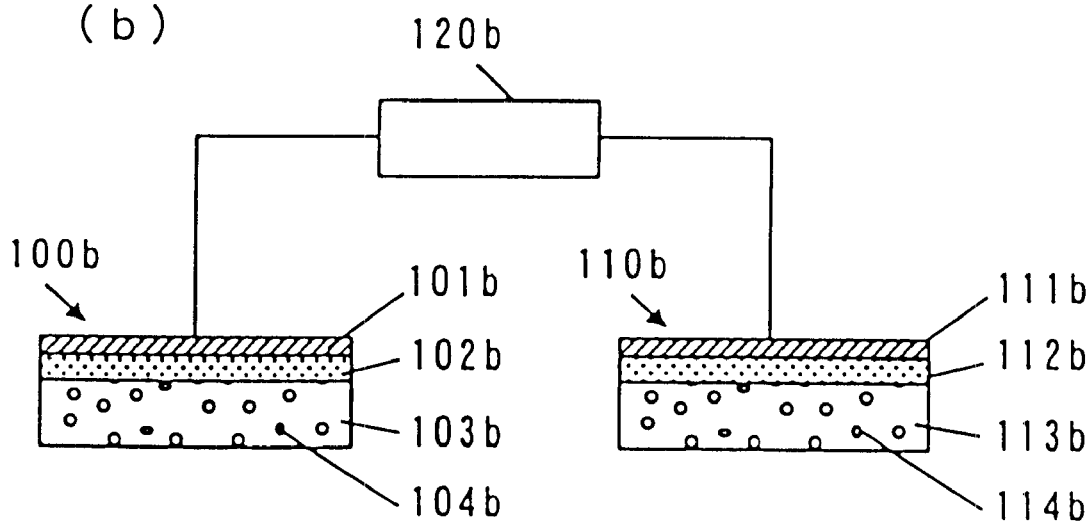

The present invention will be described in detail with reference to the drawings as necessary.

The present invention relates to a device comprising two electrode structures (the first and the second electrode structures) comprising an active electrode having the following configuration which is made of a mixture containing silver and silver chloride and a given amount of chloride ions and at least one active ingredient; and a power supply equipped with polarity inverting means in which, for inhibiting transfer of competing ions, a chloride-ion content is controlled to a level corresponding to a polarity inverting time so that a drug can be-transdermally administered with higher bioavailability and good reproductivity while maintaining effective and continuous absorption without influence of drug polarity. There are no restrictions to a method for constructing the device and reinforcing a patch, i.e., a composition, a structure, etc. of a backing.

An electrode structure used in the present invention is mainly comprised of an active electrode made of a mixture containing silver and silver chloride, a given amount of chloride ions and at least one active ingredient. Generally, the active electrode contains a substance generating a redox reaction at a voltage lower than that for electrolysis of water. It contains a substance in which eluted metal ions form an insoluble precipitate with chloride ions in the electrode structure in an anode side (e.g., silver) while contains silver chloride in a cathode side. It is, however, necessary to repeatedly continue a reversible redox reaction on the electrode surface when conducting energization by polarity inversion for a long time. In such an electrode member, there are non specific restrictions to the type of an active electrode material, but it is preferable that a reducible or oxidizable substance coexists in the electrode member in the light of energization properties and productivity. In particular, when an irreversible reaction occurs between anions extracted from the skin and silver ions in the electrode in an anode side, the content of silver in the electrode plays an important role in long-term energization. In other words, it is necessary to adjust the contents of silver and silver chloride in the electrode, depending on an energization time and a polarity inverting time. Thus, a mixture containing at least silver and silver chloride is preferable as an electrode member in the active electrode.

In the light of profitability and productivity in the present invention, an electrode member in an active electrode in the present invention is preferably prepared by printing a conductive ink. A conductive ink is mainly composed of conductive particles, a binder and a diluent. There are no restrictions to conductive particles used in the present invention as long as they are made of a mixture containing silver and silver chloride. Such an ink may be a commercially available silver-containing ink such as DW-250H-5 (manufactured by Toyo Boseki); EN-4000, EN-4040, EN-4065, EN4020, EN-4050K, EN4088A, EN-4089, EN-4072, EN4085S2, EN-4322, EN4100, EN-4117, EN-4270H, which are manufactured by Hitachi Kasei Kogyo; Electrodag 427SS, Electrodag 951SS, Electrodag 6022SS, SS24386, SS24780, SS24807, which are manufactured by Nippon Acheson; LS-504J, LS-506J, TU-1-SL, LS-005P, LS-708B, LS-411, LS-411-10, LS-3015HV, LS-3001, LS-415C-M, LS-504JM2, LS-408, which are manufactured by Asahi Chemical Institutes, to which silver chloride power is dispersed before use. A commercially available ink containing silver chloride such as JEF-314, JEF-321 series, DW2275, DB92342, DB92343 which are manufactured by Nippon Acheson may be used alone or in combination with a silver-containing ink. Furthermore, such an ink contains, for example, a graphite ink or a diluent as necessary. Since a graphite ink can reduce the content of expensive silver, it is preferable to add a graphite ink to an ink containing silver and silver chloride. The ink system may contain an additive for improving a reaction efficiency of an electrode such as surfactants, ion-exchange resins and water-soluble materials. Such a conductive ink is printed on, for example, a packing film constituting an electrode structure by an appropriate printing method such as screen printing. An electrode to be printed may have a variety of shapes such as a sheet, a mesh and a multilayer article (for example, multilayer printing where an active electrode is printed on an inactive electrode made of, for example, carbon). These may be pattern printed in a variety of shapes.

A composition ratio or mixing ratio of silver and silver chloride in the electrode member is preferably 1:9 to 9:1, more preferably 1:5 to 5:1, particularly 1:2 to 2:1. The electrode member may contain additives such as a halogenated compound such as a quaternary ammonium chloride and water-soluble or insoluble polymer/resin such as ethyl acrylate-methyl methacrylate-ethyl methacrylate trimethylammonium chloride copolymers and cholestyramine to make electrode reaction with an active electrode material more effective.

FIGS. 1 (*a*) and (*b*) show a configuration example of an iontophoresis device according to the present invention. In FIG. 1(*a*), 100*a* is the first electrode structure and 110*a* is the second electrode structure. The first electrode structure 110*a* comprises at least one active ingredient 103*a*, a hydrophilic conductive layer 102*a* containing a given amount of chloride ions and an electrode member 110*a* made of a mixture containing silver and silver chloride. The second electrode structure 110*a* is comprised of a hydrophilic conductive layer 112*a* containing at least one active ingredient 113*a* and a given amount of chloride ions and an electrode member 111*a* made of a mixture containing silver and silver chloride. A power supply 120*a* equipped with polarity inverting means for altering a current direction between the first electrode structure 100*a* and the second electrode structure 110*a* is electrically connected to the electrode members 101*a* and 111*a* a in the first and the second electrode structures, respectively. A device of the present invention may be a reservoir type structure comprising a semipermeable membrane for retaining a hydrophilic conductive layer, a selective permeable membrane for controlling transfer of substances, a control membrane for adjusting a drug permeation rate and a hydrophilic porous membrane between each hydrophilic conductive layer and the skin. Such a reservoir type structure has a structure that a pit formed on an insulating support is filled with, for example, a hydrophilic conductive layer or an electrode material, and the top surface is covered by a semipermeable membrane or a selective permeable membrane. Preferable examples of such an insulating support include, but not limited to, plastic films such as polyethylene terephthalate, polypropylene and polyethylene or metallic films such as laminated aluminum foil. Any hydrophilic or hydrophobic material which does not influence electrificity may be used as a semipermeable membrane selective permeable membrane, control membrane or hydrophilic porous membrane; for example, a variety of porous or capillary members (hereinafter, sometimes referred to as a porous material). Examples of such a porous material include organic porous materials including natural fibers such as cellulose;. semi-synthetic fibers such as cellulose acetate and nitrocellulose; a fiber assembly formed by polyethylene, polypropylene, nylon, polyester or a synthetic fiber prepared by chemical modification of these materials; a sheet such as a paper; a cloth such as fabrics and nonwoven fabrics; and porous synthetic resins such as porous polypropylene, porous polystyrene, porous poly (methyl methacrylate), porous nylon, porous polysulfones and porous fluororesins. An area of the porous material may be selected within a range where absorptivity, productivity and applicability to a living body such as skin are acceptable.

FIG. 1 (*b*) shows a configuration where an additional hydrophilic conductive layer containing chloride ions is formed under an electrode member. In this figure, 100*b* is the first electrode structure and 110*b* is the second electrode structure. The first electrode structure 100*b* is comprised of a hydrophilic conductive layer 102*b* containing a given among of chloride ions, a hydrophilic conductive layer 103*b* containing at least one active ingredient 104*b* and an electrode member 101*b* made of a mixture containing silver and silver chloride. The second electrode structure 110*b* is comprised of a hydrophilic conductive layer 112*b* containing a given amount of chloride ions, a hydrophilic conductive layer 113*b* containing at least one active ingredient 114*b* and an electrode member 111*b* made of a mixture containing silver and silver chloride. A power supply 120*b* equipped with polarity inverting means for altering a current direction between the first electrode structure 100*b* and the second electrode structure 110*b* is electrically connected to the electrode members 101*b* and 111*b* in the first and the second electrode structures, respectively. In this embodiment, a redox reaction between the electrode and chloride ions effectively proceeds.

A hydrophilic conductive layer may be of a matrix type structure in which an active ingredient is dispersed, or of a laminated structure comprising a drug retaining layer whereby the active ingredient can be applied to the skin to be in contact at a higher level. There are no restrictions to distribution of the active ingredient. A laminated structure is particularly useful when the active ingredient is chemically unstable, exhibits a potent pharmacological effect in a small amount, or is expensive. The retaining means containing the active ingredient is pressed to the hydrophilic conductive layer immediately before use. The hydrophilic conductive layer may be of, but not limited to, a gel or solution.

The hydrophilic conductive layer may be a member having a porous or capillary structure (hereinafter, sometimes referred to as a porous material) through which a drug is permeable or a combination of these. Examples of such a porous material include organic porous materials including natural fibers such as cellulose; semi-synthetic fibers such as cellulose acetate and nitrocellulose; a fiber assembly formed by polyethylene, polypropylene, nylon, polyester or a synthetic fiber prepared by chemical modification of these materials; a sheet such as a paper; a cloth such as fabrics and nonwoven fabrics; and porous synthetic resins such as porous polypropylene, porous polystyrene, porous poly(methyl methacrylate), porous nylon, porous polysulfones and porous fluororesins.

The hydrophilic conductive layer may be made of hydrophilic conductive gel; for example, synthetic polymers such as polyacrylic acid, poly(sodium acrylate), methoxyethylene-maleic anhydride copolymer, methoxyethylene-maleic acid copolymer, isobutylene-maleic anhydride copolymer, isobutylene-maleic acid copolymer, N-vinylacetamide-sodium acrylate copolymer, carboxyvinyl polymer, polyvinyl alcohol, polyvinylpyrrolidone and polyacrylamide; polysaccharides such as agar, starches, mannan, xanthan gum, locust bean gum, carageenan, gellant gum, tamarind gum, curdlan, pectin, agarbse, falseleran, guar gum, alginic acid, sodium alginate, tarra gum, karaya gum, gum arabic, cellulose and their derivatives; and gellatins, which may be used alone or in combination of two or more. A device of the present invention may appropriately contain additives such as electrolytes, pH regulators, buffers, skin protective agents, torpents, stabilizers, thickeners, wetting agents, surfactants, solubilizing agents, dissolution aids, moisturizing agents, absorption enhancing agents, adhesives, tackifiers and antiseptics as long as they do not affect device performance.

Voltage or current output from a power supply equipped with polarity inverting means according to the present invention may be generally controlled by a constant-current or constant-voltage system, but for controlling drug absorption constant current control is preferable. Current as used herein refers to transmitted current associated with drug absorption. Current output from the power supply equipped with polarity inverting means may be direct current, pulse direct current or pulse depolarized direct current. A power supply may be that which can apply continuous dc voltage or pulse dc voltage, more preferably pulse dc voltage or a combination thereof. Intermittent energization where energization and non-energization are defined in a certain way may be employed. Most preferably, a power supply which can apply square or rectangular pulse dc voltage is used. A frequency of pulse dc voltage may be appropriately selected from the range of preferably 0.1 to 200 kHz, more preferably 1 to 100 kHz, particularly 5 to 80 kHz. A ratio between ON/OFF in pulse dc voltage may be appropriately selected from the range of 1/100 to 20/1, preferably 1/50 to 15/1, more preferably 1/30 to 10/1. In polarity inverting type energization, it is necessary to avoid irritation associated with rapid current variation at the time of energization initiation, energization termination or polarity inversion. It may be achieved by conducting energization gradually varying current or voltage to a given value (for example, current is linearly or non-linearly varied at a current-application rate of 5.0 mA/min/cm$^2$ or less, preferably 2.0 mA/min/cm$^2$ or less, more preferably 0.5 mA/min/cm$^2$ or less). Polarity inverting type energization may be safely conducted by combining depolarization of a circuit during polarity inversion after energization for a given period and conducting energization by inverting polarity after a certain non-energization period (e.g., 1 $\mu$sec to 30 min, preferably 1 msec to 15 min, more preferably 10 msec to 10 min) for avoiding irritation due to skin polarization during energization or effects on drug absorption during inverting polarity. An average current density may be, but not limited to, 0.5 mA/cm$^2$ or less, preferably 0.1 mA/cm$^2$ or less, more preferably 0.05 mA/cm$^2$ or less.

Figure 2:
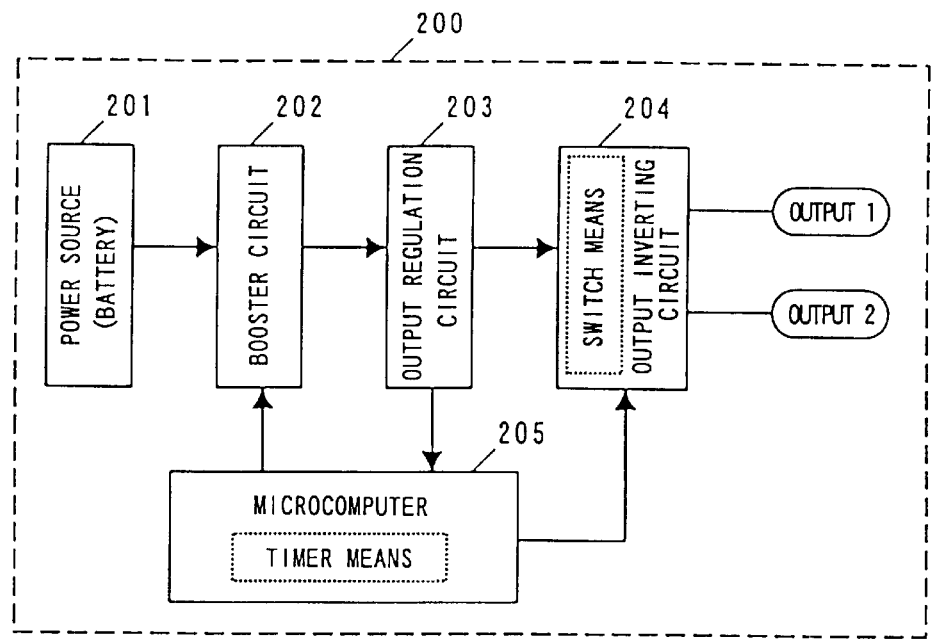
FIG. 2 shows a configuration example of a power supply used in this device.

FIG. 2 shows a configuration example of a power supply used in a device according to the present invention. As illustrated in the figure, a power supply 200 comprises a power source (battery) 201, a booster circuit 202, an output regulation circuit 203, an output inverting circuit 204 and a microcomputer 205. The output inverting circuit 204 has switch means for switching polarity. The microcomputer 205 is equipped with timer means for controlling a polarity inverting time. A combination of these allows us to conduct depolarization of a circuit during polarity inversion after energization for a given period or energization by inverting polarity after a certain non-energization period.

Figure 3:
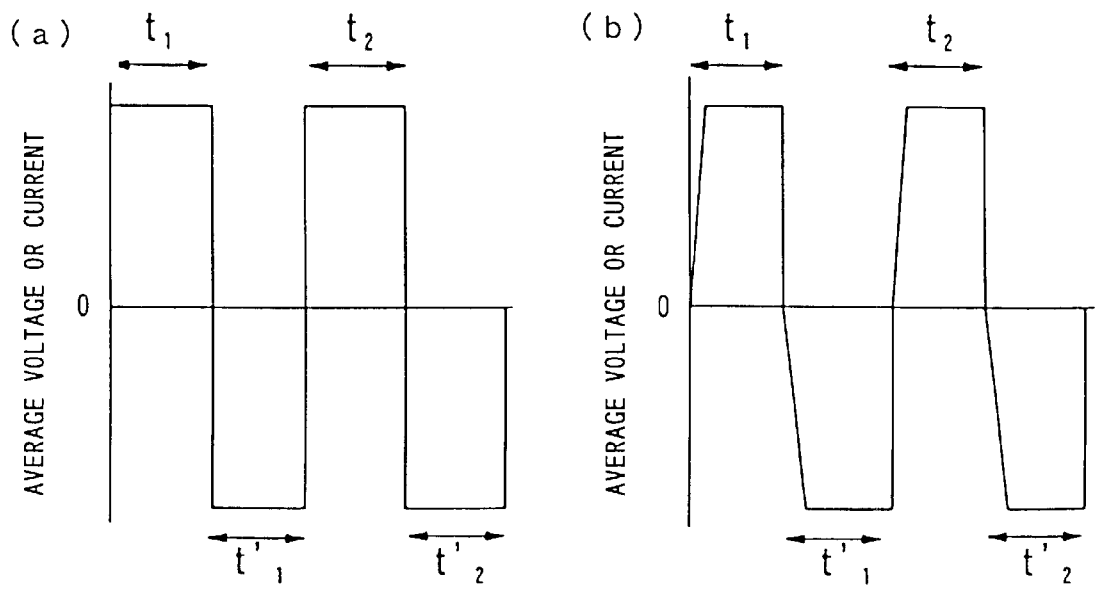
FIGS. 3 (*a*) and (*b*) show an average polarity inverting type voltage output from a power supply and a current output pattern in the present invention, respectively.

FIGS. 3 (a) and (b) show average voltage and current output patterns of the polarity-inverting type outputted from a power supply according to the present invention respectively. A polarity inverting time as used herein refers to a time from energization initiation to polarity inversion (t), a time from the inversion to the next polarity inversion (t') and each time for such a repeated operation ($t_1, t_2, \ldots t_n$, and $t'_1, t'_2, \ldots t'_n$). There are no specific restrictions to a polarity inverting time. It is, however, necessary to set an inverting time in which energization does not cause abnormal electric properties, i.e., polarity must be inverted within a range in which voltage does not rise such that problems occur in insulation or performance. It must be avoided to set an inverting time so short that drug absorptivity is adversely affected. Such a polarity inverting time is generally 1 sec to 12 hours, preferably 1 min to 6 hours, more preferably 1 min to 2 hours, depending on the state of an electrode to be printed. When a drug is anionic, chloride ions added or eluted from a cathode during energization substantially become competing ions to the drug. Their influence must be, therefore, minimized. For the purpose of such minimization, a polarity inverting time for the anionic drug may be further reduced to 1 min to 2 hours, preferably 1 min to 1 hour, more preferably 1 min to 30 min. Each polarity inverting time may be appropriately selected, but preferably the sums of the inverting times, i.e. $\Sigma Tn$ and $\Sigma T'n$, are substantially equal. More preferably, polarity inversion is repeated with regular intervals. The number of polarity inversion is generally at least one, preferably 1 to 5000, more preferably 1 to 2000. A total energization time is generally 30 min to 72 hours, preferably 2 hours to 48 hours.

The hydrophilic conductive layer in each electrode structure contains a given amount of chloride ions (a given amount as used herein refers to the amount of chloride ions contained before energization) and is electrified by a polarity-inverting type power supply. Such a given amount for chloride ions is calculated from Faraday's law. In general, a molar number (M) of a material moved by electricity can be calculated by the following equation.

$$M=(I \cdot T)/(Z \cdot F)$$

wherein I represents a current, T represents an application time, Z represents a charge number for the material and F is a constant.

A redox reaction on an electrode surface in an anode side during each inverting time in the present invention is preferably designed such that the reaction mainly involves chloride ions in the hydrophilic conductive layer.

Anode side: $Ag \rightarrow Ag^+ + e^-$  $Ag^+ + Cl^- AgCl$

A molar number of chloride ions used in a reaction during inverting time (P) is calculated by the following equation.

$$P=(I \cdot Tn)/(F) \text{ or } P'=(I \cdot T'n)/(F)$$

The amount of chloride ions corresponding to a molar number required for the redox reaction in the electrode (P: mg, molecular weight: 35.5) is represented by an average current (In: mA) and a polarity inverting time (Tn: min) depending on a polarity inverting interval. When a polarity inverting time and an average current value are appropriately selected during polarity inverting energization, the maximum required amount per one polarity inversion during an energization period is selected.

$$P=(In \times Tn \times 60 \times 35.5)/96500 = In \times Tn \times 0.022$$

On the other hand, an efficiency of the reaction between the electrode and chloride ions depends on mobility of chloride ions in a hydrophilic conductive layer. Particularly, efficiency is extremely reduced in a hydrophilic conductive layer made of a polymer base such as gel, and it is thus necessary to increase the amount of chloride ions for compensating such reduction. Drug absorptivity varies depending on mobility of ions having the same polarity as that of the drug. In other words, when the drug is anionic, chloride ions added substantially become competing ions to the drug. Chloride ions must be, therefore, used within a range in which they do not adversely affect drug absorptivity. Therefore, when a drug is neutral or cationic, a material in which competing ions to a drug are substantially immobile may be selected so that a given amount of chloride ions in the hydrophilic conductive layer can be added with no restrictions to its upper limit as long as the amount is equal to or more than the amount represented by equation (1).

$$1.0 \times (I \times T \times 0.022) \leq P \qquad \ldots (1)$$

wherein T represents a polarity inverting time (min) until polarity is inverted after energization in a certain direction and I represents an average current (mA).

On the other hand, when the drug is anionic material, chloride ions added or eluted from the electrode substantially become competing ions so that the given amount of the chloride ions must be within a range in which they do not adversely affect performance, i.e., 500-folds or less, preferably 1 to 100-folds of the amount required. The amount of chloride ions can be, therefore, represented by equation (2).

$$1.0 \times (I \times T \times 0.022) \leq P \leq 100 \times (I \times T \times 0.022) \qquad \ldots (2)$$

wherein T represents a polarity inverting time (min) until polarity is inverted after energization in a certain direction and I represents an average current (mA).

Chloride ions can be added to each electrode structure in a variety of styles. Specifically, they may be added using additives for various purposes such as electrolytes, pH regulators, buffers, skin protective agents, torpents, stabilizers, thickeners, wetting agents, surfactants, solubilizing agents, dissolution aids, moisturizing agents, absorption promoters, adhesives, tackifiers and antiseptics. For example, an additive such as an anion-exchange resin or polymer containing potassium chloride, sodium chloride, calcium chloride, glucosamine hydrochloride, triethanolamine hydrochloride, hydrochloric acid or quaternary ammonium chloride as a functional group, cholestyramine, arginine hydrochloride and an ethyl acrylate-methyl methacrylate-ethyl methacrylate trimethylammonium chloride copolymer may be added to provide chloride ions having the above function. When such an additive is used, a material having the same charge as that of drug ions which are counter ions to chloride ions (i.e., competing ions) must be used within a range where the additive does not affect absorptivity of the drug. Thus, a more preferable method for supplying chloride ions is the use of a polymer or its hydrochloride which is substantially immobile irrespective of presence or absence of hydrochloric acid, a hydrochloride of an active ingredient or energization and to which chloride ions are added. These materials may be used in combination as appropriate.

Furthermore, pH regulators or buffers may be appropriately added for adjusting pH variation caused by supplying chloride ions within a range where they do not affect drug absorption. Examples of pH regulators and additives include, but not limited to, citric acid, sodium citrate, calcium citrate, acetic acid, sodium acetate, potassium acetate, phosphoric acid, disodium hydrogenphosphate, polyphosphoric acid, potassium chloride, sodium chloride, calcium chloride, glucosamine hydrochloride, monoethanolamine, diethanolamine, triethanolamine, tromethamol, meglumine, aminoacrylate, lactic acid, sodium lactate, triethanolamine hydrochloride, hydrochloric acid, sodium hydroxide, calcium hydroxide, potassium hydroxide, polyvinylacetal diethylaminoacetate, hydroxypropylmethylcellulose, hydroxyethylcellulose phthalate, polyvinylacetate phthalate, cellulose acetate tetrahydrophthalate, and a cation exchange resin having an acetate or sulfonate group as a functional group and an anion exchange resin having quaternary ammonium group as a functional group and their salts, primary to tertiary amines or polymers/resins comprising them, cholestyramine, acidic amino acids such as aspartic acid and glutamic acid, basic amino acids such as arginine, lysine and histidine, other amino acids such as arginine hydrochloride, L-glutamine, sodium L-glutaminate, and polyamines. Particularly, organic amines, i.e., aminoacrylate, meglumine, tromethamol and triethanolamine, can be preferably used because they do not substantially affect a delivery rate of a drug administered.

Figure 4:
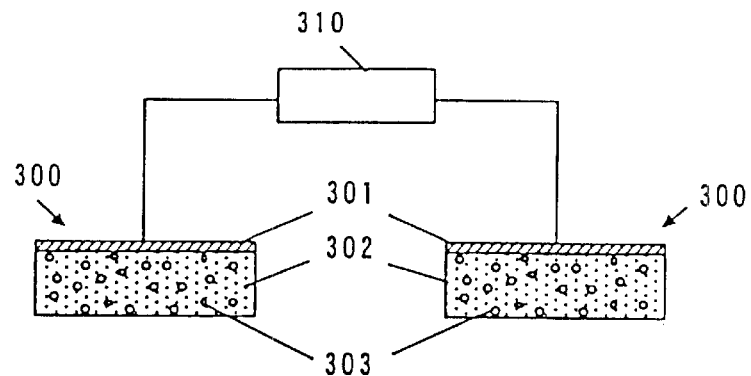
FIG. 4 shows a configuration example of an iontophoresis device according to the present invention.

When an active ingredient is cationic, a resin or polymer containing the above quaternary ammonium which does not generate ions competing the drug (for example, a cationic component from one of the above amines is substantially immobile) can be added. It is preferably added to both anode and cathode sides in the light of drug absorptivity and energization properties. FIG. 4 shows an embodiment where the electrode structures have the same configuration. When ions substantially competing with drug transfer during energization is immobile, a configuration illustrated in FIG. 4 may be employed. In FIG. 4, 300 represents two electrode structures. Each electrode structure 300 comprises a hydrophilic conductive layer 302 containing at least one active ingredient 303 and a given amount of chloride ions, and an electrode member 301 made of a mixture containing silver and silver chloride. A power supply 310 equipped with polarity inverting means for altering a current direction between the electrode structures 300 is electrically connected to the electrode members 301 in the first and the second electrode structures, respectively. The configuration is advantageous because these electrode structures can be manufactured without distinction to eliminate complexness. In other words, it is advantageous in terms of efficiency and profitability.

On the other hand, when an active ingredient is anionic, chloride ions added are substantially competing ion species having the same charge as that of the drug. Influence of such competing ion species on drug absorptivity may be minimized by (a) adding chloride ions within a range where they do not affect drug absorptivity, (b) setting a polarity inverting time to a level shorter than a general level, (c) selectively inhibiting chloride-ion transfer in a hydrophilic conductive layer, (d) adding no chloride ions to a hydrophilic conductive layer in the electrode structure whose initial polarity is the cathode side, or a combination thereof.

As described in the above (a), chloride ions may be added within a range where they do not affect drug absorptivity, using a device where chloride ions are added to the amount corresponding to a polarity inverting time in the electrode structure in FIG. 1 ($a$) or 1 ($b$) and the polarity inverting time is optimized to induce an effective redox reaction between the electrode member and the hydrophilic conductive layer containing chloride ions (for example, the amount of chloride ions added is in the range of $1.0 \times (I \times T \times 0.022) \leq P \leq 100 \times (I \times T \times 0.022)$ and the total amount is set to a value as low as possible.

As described in the above (b), a polarity inverting time may be set to a level shorter than usual, for example, 1 min to 30 min, to reduce the total amount of chloride ions added.

Selective inhibition of chloride-ion transfer in a hydrophilic conductive layer described in the above (c) may be conducted using a device where an anionic polymer is used as a hydrophilic conductive layer to prevent the chloride ions from transferring by means of electrical repulsion. Examples of such an anionic polymer include synthetic acidic polymers such as polyacrylic acid, poly(sodium acrylate), methoxyethylene-maleic anhydride copolymers, methoxyethylene-maleic acid copolymers, isobutylene-maleic anhydride copolymer, isobutylene-maleic acid copolymers, carboxyvinyl polymers and cation exchange resins containing sulfonic acid as a functional group; polysaccharides such as alginic acid, sodium alginate, carboxycellurose and carboxymethylcellulose; and proteins such as gelatins. These may be used alone or in combination thereof. The device structure illustrated in FIG. 1 ($b$) may be used to further improve an efficiency.

Figure 5:
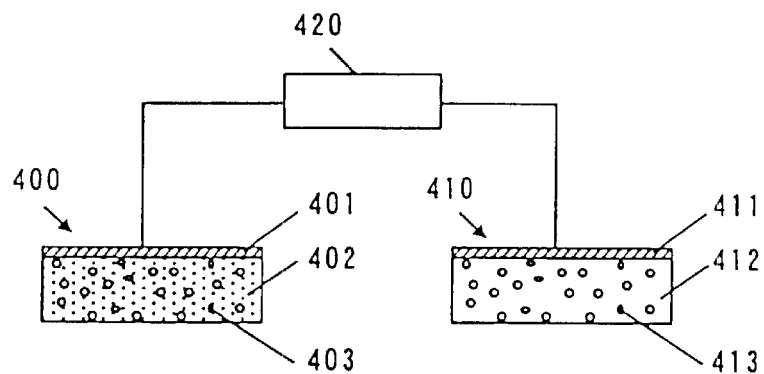
FIG. 5 shows another configuration example of an iontophoresis device according to the present invention.

As described in above (d), a device illustrated in FIG. 5 may be used for eliminating chloride ions to a hydrophilic conductive layer in an electrode structure in which the initial polarity is a cathode side. In FIG. 5, 400 represents the first electrode structure and 410 represents the second electrode structure. The first electrode structure 410 comprises a hydrophilic conductive layer 402 containing at least one active ingredient 403 and a given amount of chloride ions, and an electrode member 401 made of a mixture containing silver and silver chloride. The second electrode structure 410 comprises a hydrophilic conductive layer 412 containing at least one active ingredient 413 and an electrode member 411 made of a mixture containing silver and silver chloride. A power supply 420 equipped with polarity inverting means for altering a current direction between the first electrode structure 400 and the second electrode structure 410 is electrically connected to the electrode members 401 and 411 in the first and the second electrode structures, respectively. In such a device, the electrode structure in the cathode side does not contain ion species competing with a drug at the initiation of energization so that a higher drug utilization factor may be expected. On the other hand, transfer of chloride ions gradually eluted from the electrode in the hydrophilic conductive layer may be optimized by adjusting a transfer inhibiting method and a polarity inverting time to design a more effective device.

These may be combined to also minimize influence of competing ions (particularly, chloride ions) to an anionic drug so that absorption can be strictly controlled for a long time.

In terms of an active ingredient used in the present invention, there are no restrictions to the type of the drug, the type of its salt, indications of the drug, etc. Examples of a drug include antibiotics, antifungal agents, antitumor agents, cardiotonics, antiarrhythmic agents, vasodilators, antihypertensive agents, diuretics, hypotensive diuretics, circulatory drugs, antiplatelet drugs, hemostatic drugs, antihyperlipidaemic drugs, antipyretics, analgesics, anti-inflammatory agents, antirheumatic drugs, relaxants, antiussive expectorant drugs, antiulcer agents, sedatives, antiepileptics, antidepressants, antiallergic agents, antidiabetic drugs, antituberculous drugs, hormones, narcotic antagonists, bone resorption inhibitors, vascularization inhibitors and local anesthetics. In a preferable use of the present invention, an active ingredient may be used as a free compound rather than a salt, but it may be used as a pharmaceutically acceptable salt. Examples of a salt of a basic drug include, but not limited to, hydrochloride, sulfate, nitrate, phosphate, maleate, fumarate, tartrate, acetate, lactate, citrate, mesylate, phthalate, oxalate, malate, succinate, methanesulfonate, gluconate and enanthate. Examples of a salt of an acidic drug include, but not limited to, tromethamine, ammonium, diethylammonium and epolamine salts. Among these, a hydrochloride of a basic drug is preferable in a device of the present invention. There are no restrictions to the type or the number of an active index contained in each electrode structure, and different active ingredients may be used in the electrode structures for improving pharmacological effect. A more preferable embodiment is a device where two electrode structures contain at least one identical active ingredient.

As the antibiotic, for example, gentamycin sulfate, lipidomycin, sisomycin sulfate, tetracycline hydrochloride, ampicillin, cephalothin sodium, cefotiam hydrochloride, cefazolin sodium, thienamycin, sulfazecin, streptomycin sulfate, kanamycin sulfate, rifampicin, vancomycin hydrochloride, of loxacin and cefoceris sulfate, etc. may be used.

As the antifungal agent, for example, amphotericin B, itraconazole, fluconazole, miconazole and 2-[(1R,2R)-2-(2, 4-difluorophenyl-2-hydroxy-1-methyl-3-(1H-1,2,4-triazol-1-yl)propyl)-4-[4-(2,2,3,3-tetrafluoropropoxy)phenyl]-3-(2H,4H)-1,2,4-triazolone, etc. may be used.

As the antitumor agent, for example, bleomycin hydrochloride, tegafur, actinomycin D, mitomycin C, adriamycin, fluorouracil, 6-mercaptopurine, cytarabine, procarbazine, doxorubicin hydrochloride, methotrexate and tamoxifen citrate, etc. may be used.

As the antituberculous drug, for example, streptomycin sulfate, kanamycin sulfate, isoniazid, ethambutol hydrochloride and pyrazinamide, etc. may be used.

As the cardiotonic, for example, trans-bioxocamphor, theophilol, dopamine hydrochloride, dobutaminehydrochlbride and ubidecarenone, etc. may be used.

As the antiarrhythmic agent, for example, propranolol hydrochloride, oxyprenol hydrochloride, procainamide hydrochloride, lidocaine, phenytoin, metoprolol tartarate, verapamil hydrochloride and diltiazem hydrochloride, etc. may be used.

As the vasodilator, for example, oxyfedrine hydrochloride, tolazoline hydrochloride, pamethan hydrochloride, nicardipine hydrochloride, verapamil hydrochloride and papaverine hydrochloride, etc. may be used.

As the antihypertensive agent, for example, hydralazine hydrochloride, budralazine, prazosin hydrochloride, doxazosin mesylate, carteolol hydrochloride, clonidine hydrochloride, enalapril maleate, captopril, drapril hydrochloride, manidipine hydrochloride, pinacidil, minoxidil, rosaltan, candesaltansilexetyl, valsaltan, thermisaltan and irubesaltan, etc. may be used.

As the diuretic, for example, acetazolamide, methazolamide, chlorothiazide, furosemide, triamterene, amiloride and amin6metrozine, etc. may be used.

As the hypotensive diuretic, for example, pentolinium and hexamethonium bromide, etc. may be used.

As the circulatory drug, for example, alprostadil, rimaprost, ozagrel sodium, clopidogrel sulfate, veraprost, cyprostene, iroprost, ataprost, clinprost, ethyl icosapentoate, etilefrine hydrochloride, dihydroergotamine mesylate, pamicogrel, tranilast, probucol, candesaltansilexetyl, sodiumcitrate, DX-9065a, heparin, low molecular weight heparin, nifedipine, ehonidipine hydrochloride, diltiazem hydrochloride and tranilast, etc. may be used.

As the antiplatelet drug, for example, ticlopidine, satigrel, rimaprost-alphadex, clinprost, clopidogrelsulfate, cybrafibane, eptibatide, tirofibane hydrochloride, sulpogrelate hydrochloride, zemirofibane hydrochloride, olbofibane acetate, isbogrel, cilostazol, aspirin, abxymaba and (S)-4-(4-guanidinobenzoylamino)acetyl-3-[3-(4-guanidinobenzoylamion)]propyl-2-oxopiperadine-1-acetic acid and its salt, etc. may be used.

As the hemostatic drug, for example, epinephrine, menadione sodium bisulfite, acetomenaphthone and tranexamic acid, etc. may be used.

As the antihyperlipidaemic drug, for example, pravastatin sodium, sinvastatin, fluvastatin sodium, serivastatin and atorvastatin, etc. may be used.

As the antipyretic, analgesic or anti-inflammatory agent, for example, aspirin, sodium salicylate, sulpyrine, indomethacin, diclofenac sodium, loxoprofen sodium, ferbinac, zaltoprofen, piroxicam, nimeslid, meroxycam, cerekisicob, tialamide, emorfazone, buprenorphine, eptazocine hydrobromide, pentazocine, butorphanol tartarate, tramazol hydrochloride, ketrolac, meperidine hydrochloride, morphine hydrochloride, morphine sulfate, hydromorphine, fentanyl citrate, fentanyl and mofezolac, etc. may be used.

As the antirheumatic drug, for example, methotrexate hydrochloride, gold sodium thiomalate, auranofin, bucillamine, D-penicillamine, actarit, lobenzarit, mizoribine, salazosulfapyridine and taclorimus hydrate, etc. may be used.

As the muscle relaxant, for example, pridinol methanesulfonate, tubocurarine chloride, eperisone hydrochloride, tizanidine hydrochloride, chlorphenesin carbamate, tolperisone hydrochloride, sodium dantrolene, baclofen and lamperisone hydrochloride, etc. may be used.

As the antiussive expectorant drug, for example, ephedrine hydrochloride, codeine phosphate, picoperidamine hydrochloride, amproxol, bromhexine hydrochloride, salbutamol sulfate, tulobuterol hydrochloride, formoterol fumarate, azelastine hydrochloride, ketotifen fumarate and picoperidamine, etc. may be used.

As the antiulcer agent, for example, ornoprostil, cimetidine, famotidine, ranitidine hydrochloride, metoclopramide, omeprazole and ransoprazole, etc. may be used.

As the sedative, for example, chlorpromazine hydrochloride, atropine sulfate and fluphenazine enanthate, etc. may be used.

As the antiepileptic, for example, phenytoin sodium and ethosuximide, etc. may be used.

As the antidepressant, for example, aminotriptilin hydrochloride, imipramine hydrochloride, clomipramine hydrochloride, desipramine hydrochloride, maprotiline hydrochloride and phenelzine sulfate, etc. may be used.

As the antiallergic agent, for example, diphenylhydramine hydrochloride, tripelenamine hydrochloride, clemizole hydrochloride, chlorpheniramine d-maleate, cyproheptadine hydrochloride, ketotifen fumarate, epinastine and taclorimus hydrate, etc. may be used.

As the antidiabetic drug, for example, glymidine sodium, glipizide, methoformin, tributamide, chlorpropamide, glybenchlomid, acetohexamide, midaglysol, glymepyrid, senaglynid, lepaglynid and pioglytazone hydrochloride, etc. may be used.

As the antituberculous drug, for example, streptomycin sulfate, kanamycin sulfate, isoniazid, ethambutol hydrochloride and pyrazinamide, etc. may be used.

As the hormone, for example, β-estradiol, testosterone enanthate, prednisolone succinate, dexamethasone sodium phosphate and methimazole, etc. may be used.

As the narcotic antagonist, for example, levallorphan tartrate, nalorphine hydrochloride, protamine and naloxone, etc. may be used.

As the bone resorption inhibitor, for example, (sulfur-containing alkyl aminomethylenebisphosphonate, laroxyphene, sodium adendronate, disodium incadronate, thibolone, simadronate, risedronate, disodium chlodronate, farecalcitriol, calcitriol, α-calcitriol, sodium didronel, ipriflavone and minodronic acid, etc. may be used.

As the vascularization inhibitor, for example, vasculariztion-inhibiting steroids (See, Science Vol. 221, p.719 (1983)), fumagiol derivatives (for example, O-monochloroacetylcarbamoylfumagiol and O-dichloroacetylcarbamoylfumagiol (See, EP Patent Applications 357061, 359036, 386667 and 415294)) , etc. may be used.

As the local anesthetic, for example, lidocaine hydrochloride, tetracaine hydrochloride, procaine hydrochloride, benzocaine hydrochloride, etidocaine hydrochloride, prilocaine hydrochloride, dibucaine hydrochloride, bupivacaine hydrochloride, cocaine hydrochloride, ethylaminobenzoate, orthocainehydrochloride, oxethazaine hydrochloride and mepivacaine hydrochloride, etc. may be used.

As the other compounds which may be used as an active ingredient, peptides, proteins and nucleic acid, and oligosaccharides which are pharmacologically active may be exemplified. Abbreviations for amino acids and peptides as used herein are based on those according to IUPAC-IUB Commission on Biochemical Nomenclature or the customary abbreviations. When an amino acid may contain optical isomers, it indicates, unless otherwise specified, an L-isomer.

As the peptide, the followings may be used:

Luteinizing hormone-releasing hormones (LH-RH) or derivatives exhibiting an action similar to that of LH-RH; for example, a polypeptide represented by formula (I):

(Pyr)Glu-R1-Trp-Ser-R2-R3-R4-Arg-Pro-R5 . . . (I)

[wherein R1 represents His, Tyr, Trp or p-NH2-Phe; R2 represents Tyr or Phe; R3 represents Gly or a D-amino acid residue; R4 represents Leu, Ile or Nle; R5 represents Gly-NH-R6 (R6 is lower alkyl group optionally having hydroxyl group) or NH-R6 (R6 is as defined above)], or its salt (See, U.S. Pat. Nos. 3,853,837, 4,008,209 and 3,972,859, GB Patent 1423083, Proceedings of the National Academy of Science Vol. 78, pp. 6509–6512 (1981)), may be used.

LH-RH antagonists; for example, a polypeptide represented by formula (II):

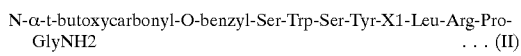

N-α-t-butoxycarbonyl-O-benzyl-Ser-Trp-Ser-Tyr-X1-Leu-Arg-Pro-GlyNH2 ... (II)

[wherein X1 represents D-Ser or D-Trp, or its salt (See, U.S. Pat. Nos. 4,086,219, 4,124,577, 4,253,997 and 4,317,815)], maybe used.

Insulin, somatostatin and somatostatin derivatives, for example, a polypeptide represented by formula (III):

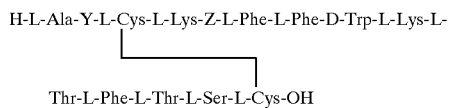

H-L-Ala-Y-L-Cys-L-Lys-Z-L-Phe-L-Phe-D-Trp-L-Lys-L- (III)

Thr-L-Phe-L-Thr-L-Ser-L-Cys-OH

[wherein Y represents D-Ala, D-Ser or D-Val; and Z represents Asn or Ala], or its salt (See, U.S. Pat. Nos. 4,087,390, 4,093,574, 4,100,117 and 4,253,998, may be used.

Adrenocorticotropic hormones (ACTH), melanocyte-stimulating hormones (MSH), thyroid stimulating hormone releasing hormones (TRH) and their derivatives, for example, a compound represented by formula (IV):

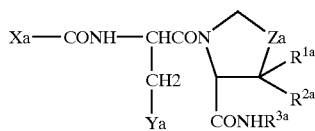

(IV)

Xa—CONH—CHCON⟨Za, R1a, R2a⟩
   |
   CH2
   |
   Ya    CONHR3a

[wherein Xa represents 4-, 5- or 6-membered heterocycle; Ya represents imidazol-4-yl or 4-hydroxyphenyl; Za represents $CH_2$ or S; $R^{1a}$ and $R^{2a}$ may be the same or different and represent hydrogen or lower alkyl group; and $R^{3a}$ represents hydrogen or optionally substituted aralkyl group], or its salt (See, Japanese Patent Laid-Open Publication Nos. 50-121273 and 52-116465), may be used.

Parathyroid hormones (PTH) and their derivatives, for example, a peptide represented by formula (V) may be used:

R1'-Val-Ser-Glu-Leu-R2'-His-Asn-R3'-R4'-R5'-His-Leu-Asn-Ser-R6'-R7'-Arg-R8'-Glu-R9'-Leu-R10'-R11'-R12'-Leu-Gln-Asp-Val-His-Asn-R13' ... (V)

[wherein R1' represents Ser or Aib; R2' represents Met or a natural lipophilic amino acid; R3' represents Leu, Ser, Lys or an aromatic amino acid; R4' represents Gly or a D-amino acid; R5' represents Lys or Leu; R6' represents Met or a natural lipophilic amino acid; R7' represents Glu or a basic amino acid; R8' represents Val or a basic amino acid; R9' represents Trp or 2-(1,3-dithiolan-2-yl)Trp; R10' represents Arg or His; R11' represents Lys or His; R12' represents Lys, Gln or Leu; R13' represents Phe or Phe-NH2], or its salt (See, Japanese Patent Laid-Open Publication Nos. 5-32696 and 4-247034, EP Patent Publications 510662, 477885 and 539491); a peptide fragment of human PTH N-terminus (1→34 position) (hereinafter, referred to as "hPTH(1→34) (See, G. W. Tregear et al., Endocrinology, 93, 1349–13543 (1973)); vasopressin and vasopressin derivatives (Desmopressin; See, Nippon Naibunpi Gakkai Zasshi, Vol. 54 (5), pp. 676–691 (1978)), may be used.

Oxytocin, calcitonin and derivatives exhibiting action similar to that of calcitonin; for example, a compound represented by formula (VI):

(VI)

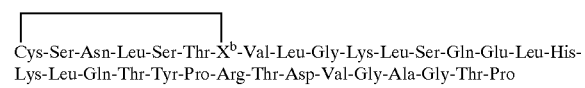

Cys-Ser-Asn-Leu-Ser-Thr-$X^b$-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro

[wherein $X^b$ represents 2-aminosuberic acid], or its salt (See, Endocrinology, 1992, 131/6 (2885–2890)); glucagon; gastrin; secretin; cholecystokinin; and angiotensin, may be used.

Enkephalin and enkephalin derivatives; for example, oligopeptides such as a peptide represented by formula (VII) may be used:

(VII)

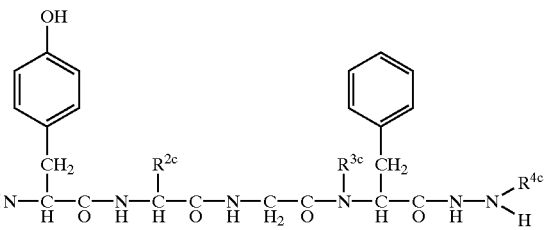

[wherein $R^{1c}$ and $R^{3c}$ represent alkyl group with 1 to 6 carbon atoms; $R^{2c}$ represents hydrogen or a D-α-amino acid; $R^{4c}$ represents hydrogen or optionally substituted with aliphatic acyl group having 1 to 8 carbon atoms], or its salt (See, U.S. Pat. No. 4,277,394, EP Patent Application Publication 31567); and endorphin, may be used.

Kyotorphin, interleukins (I to XI), tuftsin, thymopoietin, thymic humoral factor (THF), blood thymic factor (FTS) and their derivatives; for example, a peptide represented by formula (VIII):

PGlu-Xd-Lys-Ser-Gln-Yd-Zd-Ser-Asn-OH ... (VIII)

[wherein Xd represents L- or D-Ala; Yd and Zd each independently represent Gly or a D-amino acid having 3 to 9 carbon atoms], or its salt (See, U.S. Pat. No. 4,229,438); and other thymic hormones such as thymosin-α1 and -β4 and thymic factor X (See, Igaku no Ayumi, Vol. 125 (10), pp. 835–843 (1983)), may be used.

Motilin, deinorphin, bombesin, neurotensin, cerulein, bradykinin, urokinase, substance P, polymyxin B, colistin, gramicidin, bacitracin, protein synthesis stimulating peptide (See, GB Patent 8232082), gastrin release inhibiting polypeptide (GIP), vasoactive intestinal polypeptide (VIP), platelet-derived growth factor (PDGF) and growth hormone secretion factor (GRF, somatocrinin), etc. may be used.

These biologically active peptides may be derived from human or other animals such as bovine, swine, poultry, salmon and eel. These may be chimeras of those derived from human or these animals, or active derivatives in which a part of the structure has been modified. For example, insulin derived from swine, calcitonin derived from swine, poultry, salmon or eel, or chimeras of those derived from human or salmon may be used; for example, a peptide represented by formula (IX):

Cys-Gly-Asn-Leu-Ser-Thr-Cys-Met-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro  ... (IX)

(See, Endocrinology, 1992, 131/6 (2885–2890)), etc. may be used.

EXPERIMENTAL EXAMPLES

The present invention will be specifically described with reference to, but not limited to, Comparative Examples and Examples according to the following Experimental Examples. Experimental Example 1 shows in vivo evaluation for effects of an electrode material on electric properties and absorptivity in polarity inverting energization. Experimental Example 2 studies absorptivity and electric properties in a rat for an electrode structure according to the present invention. Experimental Examples 3 and 4 study absorptivity and electric properties in a rat in terms of relationship between the amount of chloride ions in a basic drug and a polarity inverting time and relationship between the amount of chloride ions in an acidic drug and a polarity inverting time, respectively. Experimental Example 5 shows an absorption test for fentanyl citrate in a rabbit using an electrode structure according to the present invention.

Experimental Example 1

In Experimental Example 1, effect of an electrode material on a device structure according to the present invention was studied. In this experiment, an abdominal skin of an SD rat (male, weight: about 250 to 300 g) was shaved with clippers and a shaver, and degreased and disinfected using sanitary cotton containing 70% aqueouse thanolforuse. Table 1 shows. electrode materials in electrode structures in Examples 1 and 2 and Comparative Example 1. Each electrode was placed in a vessel prepared by screen-printing a PET sheet with a conductive ink containing each electrode material and then molding it into a cup (PET, id: 24 mm, an effective area: 4.5 cm$^2$) and the vessel was filled with 0.7 g of a gel containing 5.0% (w/w) cholestyramine and 2.0% (w/w) lidocaine hydrochloride, 0.2% (w/w) methylparaben and 1.0% (w/w) agar to prepare an electrode structure. Two pieces of the electrode structures (the first and the second electrode structures) were attached on the rat abdominal skin and energization was conducted using pulse depolarized direct current (frequency: 50 kHz, duty: 50%) with a short circuiting switch under the conditions of a constant current: 0.1 mA/cm$^2$, a polarity inverting time: 30 min and the total energization time: 4 hours. After energization, the amount of the drug remaining in each electrode structure was determined by high performance liquid chromatography and the total drug absorption was calculated by subtracting the remaining amount from the initial content (about 24.2 mg/two pieces as lidocaine).

TABLE 1

| Experimental Example 1 | 1st electrode structure | 2nd electrode structure |
|---|---|---|
| Example 1 | Silver | Silver/Silver chloride |
| Example 2 | Silver/Silver chloride | Silver/Silver chloride |

TABLE 1-continued

| Experimental Example 1 | 1st electrode structure | 2nd electrode structure |
|---|---|---|
| Comparative Example 1 | Carbon | Carbon |

Table 2 shows the results obtained in the above Examples and Comparative Example. Using the electrode material in Example 1, there were observed momentary voltage increase at the time of polarity inversion during energization and tendency to gradual voltage increase during energization. Such variations in electric properties might be caused by gradual reduction of chloride ions (existing as silver chloride) in the electrode during energization as the cathode side in the first electrode structure. In Example 2, voltage variation during energization was not observed. On the other hand, in Comparative Example 1 using an inactive electrode, a voltage was rapidly increased during energization and then became insulated so that energization cannot be continued. In Comparative Example 1, it was caused by variation of a gel contact area due to gas generation during energization. The total absorption of lidocaine was about 3.2 to 3.4 mg in Examples 1 and 2 while being as considerably low as about 1.8 mg in Comparative Example 1.

TABLE 2

| Experimental Example 1 | Electric properties | Total absorption of lidocaine |
|---|---|---|
| Example 1 | Momentary voltage increase during polarity inversion and tendency to gradual voltage increase | about 3.4 mg |
| Example 2 | No variation | about 3.2 mg |
| Comparative Example 1 | After voltage increase, insulated state | about 1.8 mg |

Experimental Example 2

Electrode structures were prepared using formulations described in Examples 3 to 8 and Comparative Examples 2 and 3 to be evaluated for their electric properties and drug absorptivity. Each electrode was placed in a vessel prepared by screen-printing a PET sheet with a conductive ink containing silver and silver chloride (a molar ratio of silver:silver chloride was 1:1) and then molding it into a cup (PET, id: 24 mm, an effective area: 4.5 cm$^2$) and the vessel was filled with 0.7 g of a gel having each Example or Comparative Example. In this experiment, an abdominal skin of an SD rat (male, weight: about 250 to 300 g) was shaved with clippers and a shaver, and degreased and disinfected using sanitary cotton containing 70% aqueous ethanol for use. Two pieces of the electrode structures (the first and the second electrode structures) were attached on the rat abdominal skin and energization was conducted using pulse depolarized direct current (frequency: 50 kHz, duty: 50%) with a short circuiting switch under the conditions of a constant current: 0.1 mA/cm$^2$, a polarity inverting time: 30 min and the total energization time: 4 hours. After energization, the amount of the drug remaining in each electrode structure was determined by high performance liquid chromatography and the total drug absorption was calculated by subtracting the remaining amount from the initial content.

Example 3

| Ingredient | Content (% (w/w)) |
| --- | --- |
| Lidocaine hydrochloride | 2.0 |
| Agar | 1.0 |
| Methyl p-oxy p-oxybenzoate | 0.2 |
| Injectable distilled water | q.s. |
| Total | 100 |

Example 4

| Ingredient | Content (% (w/w)) |
| --- | --- |
| Lidocaine hydrochloride | 2.0 |
| Polyvinyl alcohol | 10.0 |
| Cholestyramine | 5.0 |
| Methyl p-oxy p-oxybenzoate | 0.2 |
| Injectable distilled water | q.s. |
| Total | 100 |

Example 5

| Ingredient | Content (% (w/w)) |
| --- | --- |
| Fentanyl citrate | 2.0 |
| Agar | 1.0 |
| Cholestyramine | 5.0 |
| Trometamol | 0.2 |
| Methyl p-oxybenzoate | 0.2 |
| Injectable distilled water | q.s. |
| Total | 100 |

Example 6

| Ingredient | Content (% (w/w)) |
| --- | --- |
| Fentanyl citrate | 2.0 |
| Agar | 1.0 |
| Ethyl acrylate-ethyl trimethylammonium ethyl copolymer | 5.0 |
| Trometamol | 0.2 |
| Methyl p-oxybenzoate | 0.2 |
| Injectable distilled water | q.s. |
| Total | 100 |

Example 7

| Ingredient | Content (% (w/w)) |
| --- | --- |
| Diclofenac sodium | 1.0 |
| Agar | 1.0 |
| Cholestyramine | 1.0 |
| Methyl p-oxybenzoate | 0.2 |
| Injectable distilled water | q.s. |
| Total | 100 |

Example 8

| Ingredient | Content (% (w/w)) |
| --- | --- |
| Diclofenac sodium | 1.0 |
| Polyvinyl alcohol | 10.0 |
| Cholestyramine | 1.0 |
| Methyl p-oxybenzoate | 0.2 |
| Injectable distilled water | q.s. |
| Total | 100 |

Comparative Example 2

| Ingredient | Content (% (w/w)) |
| --- | --- |
| Fentanyl citrate | 2.0 |
| Agar | 1.0 |
| Trometamol | 0.2 |
| Methyl p-oxybenzoate | 0.2 |
| Injectable distilled water | q.s. |
| Total | 100 |

Comparative Example 3

| Ingredient | Content (% (w/w)) |
| --- | --- |
| Diclofenac sodium | 1.0 |
| Agar | 1.0 |
| Methyl p-oxybenzoate | 0.2 |
| Injectable distilled water | q.s. |
| Total | 100 |

The results obtained from the above Examples and Comparative Examples are shown in Table 3. When lidocaine hydrochloride was added to a formulation as was in Example 3 or 4, chloride ions in the formulation reacted with silver ions eluted from the electrode, there was not observed skin coloration and higher absorptivity was indicated (about 17% to the dose). When fentanyl citrate was used as a drug, chloride ions in the formulation in Example 5 or 6 were supplied from the quaternary ammonium chloride so that there was not observed skin coloration after energization and higher absorptivity was indicated, i.e., about 17% to the dose. On the other hand, since there were not present chloride ions in the formulation in Comparative Example 2, silver was transferred into the gel during energization to precipitate insoluble materials and there was observed skin coloration.

When using diclofenac sodium was used as a drug, chloride ions added in Example 7 or 8 (the quaternary ammonium chloride) became a competing component, but the quaternary ammonium chloride was added to a small amount and a polarity inverting time was short, so that the results were similar to those in Comparative Example 3 (about 30% to the dose). In Comparative Example 3, there was, however, observed coloration of the skin in contact with both device structures after energization due to silver ions eluted in the anode side during energization.

TABLE 3

Experimental Example 2

| | Energization properties | Total absorption(mg)/dose(mg) | Skin irritation |
|---|---|---|---|
| Example 3 | No variation | 4.1 mg/24.2 mg lidocaine free | No variation |
| Example 4 | No variation | 4.2 mg/24.2 mg lidocaine free | No variation |
| Example 5 | No variation | 3.0 mg/17.8 mg fentanyl free | No variation |
| Example 6 | No variation | 2.9 mg/17.8 mg fentanyl free | No variation |
| Example 7 | No variation | 3.2 mg/13.0 mg diclofenac free | No variation |
| Example 8 | No variation | 4.6 mg/13.0 mg diclofenac free | No variation |
| Comparative Example 2 | No variation | 5.2 mg/17.8 mg fentanyl free | Coloration |
| Comparative Example 3 | Voltage increase during energization | 3.7 mg/13.0 mg diclofenac free | Coloration |

Experimental Example 3

Using fentanyl citrate as a basic drug, electrode structures were prepared from the formulas described in Examples 9 to 14 and Comparative Examples 4 and 5 for evaluating relationship between a chloride ion content and a polarity inverting time from electric properties and drug absorptivity. Each electrode was placed in a vessel prepared by screen-printing a PET sheet with a conductive ink containing silver and silver chloride (a molar ratio of silver:silver chloride was 1:1) and then molding it into a cup. (PET, id: 24 mm, an effective area: 4.5 cm$^2$) and the vessel was filled with 0.7 g of a gel having each Example or Comparative Example. In this experiment, an abdominal skin of an SD rat (male, weight: about 250 to 300 g) was shaved with clippers and a shaver, and degreased and disinfected using sanitary cotton containing 70% aqueous ethanol for use. Two pieces of the electrode structures (the first and the second electrode structures) were attached on the rat abdominal skin and energization was conducted using pulse depolarized direct current (frequency: 50 kHz, duty: 50%) with a short circuiting switch under the conditions of a constant current: 0.1 mA/cm$^2$, a polarity inverting time: 30 sec to 90 min and the total energization time: 4 hours. After energization, the amount of the drug remaining in each electrode, structure was determined by high performance liquid chromatography and the total drug absorption was calculated by subtracting the remaining amount from the initial content. Table 4 shows a chloride ion content and a polarity inverting time for each Example or Comparative Example. A chloride ion content in each electrode structure in this experiment was calculated from a chloride ion content (about 15% (w/w)) in cholestyramine. A ratio of an added chloride ion amount to a required chloride ion amount (P) was estimated from the required chloride ion amount calculated from a chloride ion content in each electrode structure and the amount of chloride ions reacted in a predetermined polarity inverting time.

Example 9

| Ingredient | Content (% (w/w)) |
|---|---|
| Fentanyl citrate | 2.0 |
| Agar | 1.0 |
| Cholestyramine | 1.0 |
| Tromethamol | 0.2 |
| Methyl p-oxybenzoate | 0.2 |
| Injectable distilled water | q.s. |
| Total | 100 |

Example 10

| Ingredient | Content (% (w/w)) |
|---|---|
| Fentanyl citrate | 2.0 |
| Agar | 1.0 |
| Cholestyramine | 3.0 |
| Tromethamol | 0.2 |
| Methyl p-oxybenzoate | 0.2 |
| Injectable distilled water | q.s. |
| Total | 100 |

Example 11

| Ingredient | Content (% (w/w)) |
|---|---|
| Fentanyl citrate | 2.0 |
| Agar | 1.0 |
| Cholestyramine | 5.0 |
| Tromethamol | 0.2 |
| Methyl p-oxybenzoate | 0.2 |
| Injectable distilled water | q.s. |
| Total | 100 |

Examples 12 to 14 and Comparative Examples 4 and 5

| Ingredient | Content (% (w/w)) |
|---|---|
| Fentanyl citrate | 2.0 |
| Agar | 1.0 |
| Cholestyramine | 10.0 |
| Tromethamol | 0.2 |

-continued

| Ingredient | Content (% (w/w)) |
|---|---|
| Methyl p-oxybenzoate | 0.2 |
| Injectable distilled water | q.s. |
| Total | 100 |

TABLE 4

Experimental Example 3

| | Chloride ion content in one electrode structure | Ratio of add. Cl/req. Cl ions | Polarity inverting time |
|---|---|---|---|
| Example 9 | about 1.1 mg (cholestyramine 7 mg) | about 4 times | 30 min |
| Example 10 | about 3.2 mg (cholestyramine 21 mg) | about 11 times | 30 min |
| Example 11 | about 5.3 mg (cholestyramine 35 mg) | about 18 times | 30 min |
| Example 12 | about 11.0 mg (cholestyramine 70 mg) | about 1111 times | 1 min |
| Example 13 | about 11.0 mg (cholestyramine 70 mg) | about 19 times | 60 min |
| Example 14 | about 11.0 mg (cholestyramine 70 mg) | about 12 times | 90 min |
| Comparative Example 4 | about 11.0 mg (cholestyramine 70 mg) | about 2222 times | 0.5 min |
| Comparative Example 5 | about 11.0 mg (cholestyramine 70 mg) | about 5 times | 240 min |

Table 5 shows absorption amounts in a rat for a basic drug (fentanyl citrate) for the above Examples and Comparative Examples. In Examples 9 to 14, an absorption amount for fentanyl was about 2.0 to 4.4 mg, which corresponded to about 15%. In the range of a chloride ion amount added to a formulation in this experiment (about 1111 folds to the required chloride ion amount corresponding to a polarity inverting time), any Example showed high absorptivity and there was not observed voltage variation during energization.

On the other hand, effect of a polarity inverting time on absorptivity for fentanyl chloride and electric properties was studied in Examples 12 to 14 and Comparative Examples 4 and 5, indicating that absorptivity was reduced in Comparative Example 4 where a polarity inverting time was short (0.5 min). In particular, in Comparative Example 5, voltage increase was observed and the structure became insulated during energization. On the other hand, in the range of a polarity inverting time in Examples 9 and 14, there were no significant variations although there was observed tendency to voltage increase in Example 14.

TABLE 5

Experimental Example 3

| | Energization properties | Total absorption(mg)/dose(mg) |
|---|---|---|
| Example 9 | No variation | 2.5 mg/17.8 mg fentanyl free |
| Example 10 | No variation | 4.4 mg/17.8 mg fentanyl free |
| Example 11 | No variation | 2.6 mg/17.8 mg fentanyl free |
| Example 12 | No variation | 2.0 mg/17.8 mg fentanyl free |
| Example 13 | No variation | 2.3 mg/17.8 mg fentanyl free |
| Example 14 | Tendency to voltage increase | 2.3 mg/17.8 mg fentanyl free |

TABLE 5-continued

Experimental Example 3

| | Energization properties | Total absorption(mg)/dose(mg) |
|---|---|---|
| Comparative Example 4 | No variation | 1.1 mg/17.8 mg fentanyl free |
| Comparative Example 5 | Voltage increase during energization and insulation | — |

Experimental Example 4

Using diclofenac sodium as an acidic drug, electrode structures were prepared from the formulas described in Examples 15 to 19 and Comparative Examples 6 and 7 for evaluating relationship between a chloride ion content and a polarity inverting time from electric properties and drug absorptivity. Each electrode was placed in a vessel prepared by screen-printing a PET sheet with a conductive ink containing silver and silver chloride (a molar ratio of silver:silver chloride was 1:1) and then molding it into a cup (PET, id: 24 mm, an effective area: 4.5 cm$^2$) and the vessel was filled with 0.7 g of a gel having each Example or Comparative Example. In this experiment, an abdominal skin of an SD rat (male, weight: about 250 to 300 g) was shaved with clippers and a shaver, and degreased and disinfected using sanitary cotton containing 70% aqueous ethanol for use. Two pieces of the electrode structures (the first and the second electrode structures) were attached on the rat abdominal skin and energization was conducted using pulse depolarized direct current (frequency: 50 kHz, duty: 50%) with a short circuiting switch under the conditions of a constant current: 0.1 mA/cm$^2$, a polarity inverting time: 30 sec to 90 min and the total energization time: 4 hours. After energization, the amount of the drug remaining in each electrode structure was determined by high performance liquid chromatography and the total drug absorption was calculated by subtracting the remaining amount from the initial content. Table 6 shows a chloride ion content and a polarity inverting time for each Example or Comparative Example. A chloride ion content in each electrode structure in this experiment was calculated from a chloride ion content (about 15% (w/w)) in cholestyramine. A ratio of an added chloride ion amount to a required chloride ion amount (P) was estimated from the required chloride ion amount calculated from a chloride ion content in each electrode structure and the amount of chloride ions reacted in a predetermined polarity inverting time.

Example 15

| Ingredient | Content (% (w/w)) |
|---|---|
| Diclofenac sodium | 1.0 |
| Agar | 1.0 |
| Cholestyramine | 1.0 |
| Methyl p-oxybenzoate | 0.2 |
| Injectable distilled water | q.s. |
| Total | 100 |

Example 16

| Ingredient | Content (% (w/w)) |
|---|---|
| Diclofenac sodium | 1.0 |
| Agar | 1.0 |
| Cholestyramine | 5.0 |
| Methyl p-oxybenzoate | 0.2 |
| Injectable distilled water | q.s. |
| Total | 100 |

Example 17

| Ingredient | Content (% (w/w)) |
|---|---|
| Diclofenac sodium | 1.0 |
| Agar | 1.0 |
| Cholestyramine | 7.5 |
| Methyl p-oxybenzoate | 0.2 |
| Injectable distilled water | q.s. |
| Total | 100 |

Example 18

| Ingredient | Content (% (w/w)) |
|---|---|
| Diclofenac sodium | 1.0 |
| Agar | 1.0 |
| Cholestyramine | 0.1 |
| Methyl p-oxybenzoate | 0.2 |
| Injectable distilled water | q.s. |
| Total | 100 |

Example 19

| Ingredient | Content (% (w/w)) |
|---|---|
| Diclofenac sodium | 1.0 |
| Agar | 1.0 |
| Cholestyramine | 12.5 |
| Methyl p-oxybenzoate | 0.2 |
| Injectable distilled water | q.s. |
| Total | 100 |

Comparative Example 6

| Ingredient | Content (% (w/w)) |
|---|---|
| Diclofenac sodium | 1.0 |
| Agar | 1.0 |
| Cholestyramine | 10.0 |
| Methyl p-oxybenzoate | 0.2 |
| Injectable distilled water | q.s. |
| Total | 100 |

Comparative Example 7

| Ingredient | Content (% (w/w)) |
|---|---|
| Diclofenac sodium | 1.0 |
| Agar | 1.0 |
| Cholestyramine | 0.05 |
| Methyl p-oxybenzoate | 0.2 |
| Injectable distilled water | q.s. |
| Total | 100 |

TABLE 6

| Experimental Example 4 | Chloride content in one electrode structure | Ratio of add. Cl/req. Cl ions | Polarity inverting time |
|---|---|---|---|
| Example 15 | about 1.2 mg (cholestyramine 8 mg) | about 12 times | 10 min |
| Example 16 | about 6.0 mg (cholestyramine 40 mg) | about 60 times | 10 min |
| Example 17 | about 9.0 mg (cholestyramine 60 mg) | about 90 times | 10 min |
| Example 18 | about 0.12 mg (cholestyramine 0.8 mg) | about 12 times | 1 min |
| Example 19 | about 15.0 mg (cholestyramine 100 mg) | about 12 times | 120 min |
| Comparative Example 6 | about 12.0 mg (cholestyramine 80 mg) | about 120 times | 10 min |
| Comparative Example 7 | about 0.06 mg (cholestyramine 0.4 mg) | about 12 times | 0.5 min |

Table 7 shows energization properties and absorption amounts in a rat for an acidic drug (diclofenac sodium) for the above Examples and Comparative Examples. In Examples 15 to 19, an absorption amount for fentanyl was 4.2 to 6.3 mg, which corresponded to about 40%. In the range of a chloride ion amount added to a formulation in this experiment (about 11 to 80 folds to the required chloride ion amount corresponding to a polarity inverting time), any Example showed high absorptivity and there was not observed voltage variation during energization. In Comparative Example 6 where an about 111-folds of chloride ions were present, there was observed tendency to absorption reduction.

On the other hand, effect of a polarity inverting time was studied in Examples 15, 18 and 19 and Comparative Example 7, indicating that absorptivity tended to be reduced in Comparative Example 7 where a polarity inverting time was short (0.5 min). In Examples 15 to 18 and Comparative Examples 6 and 7, there was not observed voltage variation while there was observed tendency to voltage increase during energization in Example 19.

TABLE 7

Experimental Example 4

| | Energization properties | Total absorption(mg)/dose(mg) |
|---|---|---|
| Example 15 | No variation | 5.8 mg/13.0 mg diclofenac free |
| Example 16 | No variation | 5.6 mg/13.0 mg diclofenac free |
| Example 17 | No variation | 6.1 mg/13.0 mg diclofenac free |
| Example 18 | No variation | 4.2 mg/13.0 mg diclofenac free |
| Example 19 | Tendency to voltage increase | 6.3 mg/13.0 mg diclofenac free |
| Comparative Example 6 | No variation | 3.1 mg/13.0 mg diclofenac free |
| Comparative Example 7 | No variation | 3.5 mg/13.0 mg diclofenac free |

Experimental Example 5

Using fentanyl citrate as a basic drug, an electrode structure was prepared from the formula described in Example 20 for determining continuous absorptivity for a long period in a polarity inverting energization in an absorption test on a rabbit. The electrode was placed in a vessel prepared by screen-printing a PET sheet with a conductive ink containing silver and silver chloride (a molar ratio of silver:silver chloride was 1:1) and then molding it into a cup (PET, id: 24 mm, an effective area: 4.5 cm$^2$) and the vessel was filled with 0.7 g of a gel having each Example or Comparative Example. In this experiment, a back skin of a Japanese white male rabbit (weight: about 3.0 to 4.0 kg) was shaved with clippers and a shaver, and degreased and disinfected using sanitary cotton containing 70% aqueous ethanol for use. Two pieces of the electrode structures (the first and the second electrode structures) were attached on the rabbit back skin and energization was conducted using pulse depolarized direct current (frequency: 50 kHz, duty: 50%) with a short circuiting switch under the conditions of a constant current: 0.1 mA/cm$^2$, a polarity inverting time: 30 min and the total energization time: 8 hours. At regular intervals, blood was sampled from an auricular vein to determined a concentration of drug in serum by GC-MS.

Example 20

| Ingredient | Content (% (w/w)) |
|---|---|
| Fentanyl citrate | 2.0 |
| Agar | 1.0 |
| Cholestyramine | 3.0 |
| Tromethamol | 0.2 |
| Methyl p-oxybenzoate | 0.2 |
| Injectable distilled water | q.s. |
| Total | 100 |

Figure 6:
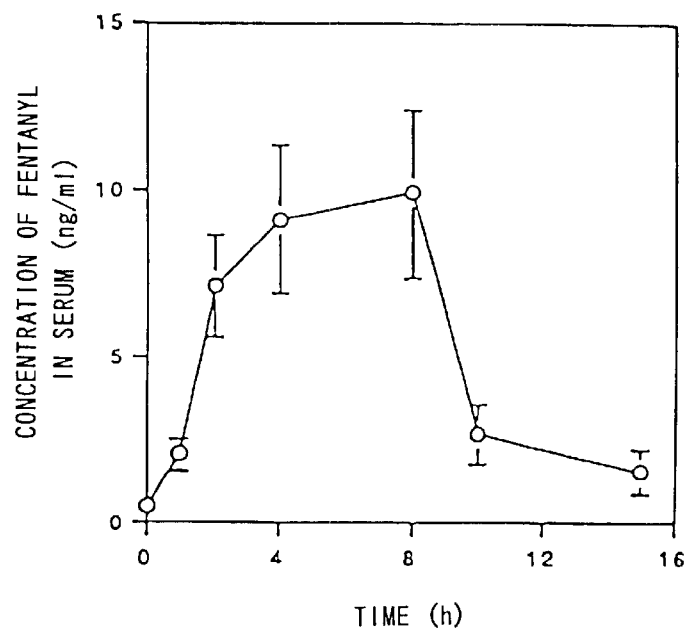
FIG. 6 is a graph illustrating a concentration of fentanyl in serum during polarity inverting type energization in Example 20.

FIG. 6 shows a concentration of fentanyl in serum when polarity inverting energization was conducted for 8 hours using the electrode structure in FIG. 20. A concentration of fentanyl in serum was maintained to about 10 to 15 ng/ml for a long period during energization. Skin irritation was not observed in the device-attachment site at the completion of energization. These results confirmed that polarity inverting energization using an electric structure according to the present invention can administer a drug continuously and safely during long-term use.

Preparation Example

Preparation of (S)-4-(4-guanidinebenzoylamino)acetyl-3-[3-(4-guanidinebenzoylamino)]propyl-2-oxopiperadine-1-acetic acid bishydrochloride

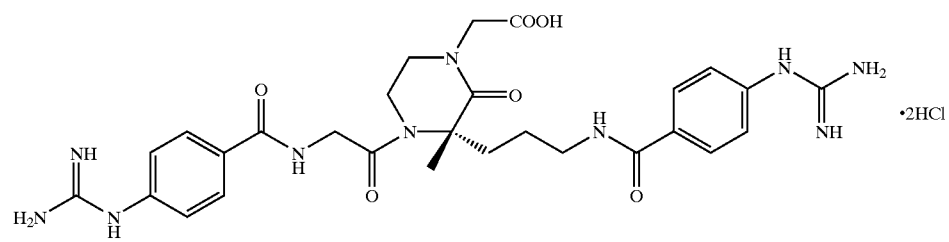

To an aqueous solution of (S)-4-aminoacetyl-3-(3-aminopropyl)-2-oxo-piperadine-1-acetic acid (GAPA) were added 7.0 L of acetonitrile, 6.6 L of water and 448 g of sodium hydrogen carbonate (5.33 mol), then 1607 g of N-(4-guanidinobenzoyloxy)-5-norbornene-2,3-dicarboxyimide (GBNB) (4.27 mol) was added, and then the mixture was stirred at room temperature for 4 hours. The reaction was adjusted to pH3 with 2N HCl and extracted with ethyl acetate (30 L×3). The aqueous layer was concentrated in vacuo to about 10 L. Ten liters of water was added and the mixture was adjusted to pH5.0 with sodium hydrogen carbonate. The mixture was absorbed by a resin (SP-207, 30 L filled column). The column was washed with 150 L of pure water, and then eluted with 250 L of 0.003N HCl/5% acetonitrile. Effective fractions (about 200 L) were combined and concentrated in vacuo to about 10 L. The concentrate was adjusted to pH1.5 with conc. hydrochloric acid (about 117 ml) and further concentrated to 3 L. To the concentrate was added 24 L of ethanol. The mixture was stirred at room temperature for 19 hours and then under ice-cooling for 2 hours, and precipitated crystals were collected. The crystals were washed with 900 ml of 89% ethanol, air-dried overnight, dried in vacuo at 50° C. for 9 hours to give 819 g of crude crystals of the desired compound. The crude crystals were dissolved in 2.05 L of water and to the mixture was added 16.5 g of charcoal. The mixture was stirred at room temperature for 30 min and then filtered. The filtrate was passed through a 0.2 $\mu$ membrane filter and to the filtrate was added 20.5 L of ethanol. After stirring at room temperature for 5 hours and then under ice-cooling for 2 hours, precipitated crystals were collected. The crystals were washed with 89% ethanol (1.0 L), dried in vacuo at 50° C. for 9 hours, humidified overnight (RH 100%), again dried in vacuo at 50° C. for 9 hours and left at RH 60 to 70% for about 3 days to give 753 g of purified crystals of the desired compound (bishydrochloride) containing 5% water (about 2 mol).

Melting point: 245 to 251.5° C.

Analysis for $C_{27}H_{34}N_{10}O_6$—$2HCl$–$1.5H_2O$

Calcd.: C, 46.69; H, 5.66; N, 20.17; Cl, 10.21

Observed: C, 46.15; H, 5.62; N, 19.94; Cl, 10.65

Example 21

Figure 7:
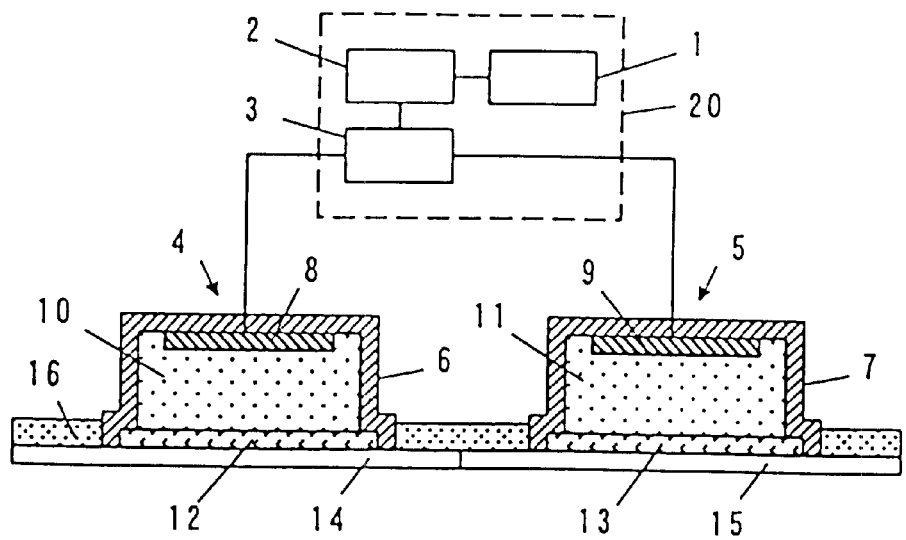
FIG. 7 is a cross section illustrating a specific configuration example of an iontophoresis device according to the present invention.

An iontophoresis delivery device as illustrated in FIG. 7 was prepared, which contained the compound prepared in Preparation Example in conducting media 10, 11. Any device used in an iontophoresis transdermal permeation process in the present invention may be used as long as it meets requirements for switching iontophoresis transdermal delivery. As illustrated in FIG. 7, it may comprise, but not limited to, a power source 1, a power supply 20 having a computer-controlled current generator 2 and a timer-equipped switch 3, two electrode device units 4, 5, an adhesive tape 16 and peeling liners 14, 15. Each of these electrode device units 4, 5 comprises, for example, a concave insulating support 6, 7, an electrode 8, 9, a conductive medium layer 10, 11, (for example, a conductive water reservoir containing hydrogel, an electrolyte, etc.) and a hydrophilic porous membrane 12, 13.

The paired two electrode device units 4, 5 had the same disk figure where the inner diameter of the electrodes 8, 9 was 25 mm; the inner diameter and the volume of the conductive media 10, 11 were 30 mm and 1.3 ml, respectively; and the diameter of the hydrophilic porous membrane 12, 13 was 35 mm (corresponding to a surface area of 9.62 cm$^2$). The insulating support 6, 7 was a plastic (polyethylene terephthalate: PET) cup (an eaves length: about 5 mm). The electrode was that in which silver and silver chloride was printed on a sheet with a weight ratio of 1:1. The thickness of silver/silver chloride printed was about 15 $\mu$m. The conductive medium was a gel containing 4.32% (w/w) of the above compound (corresponding to 56.13 mg as a 2HCl salt or 50 mg as a free compound), 1% (w/w) of agarose, 10% (w/w) of L-proline and 0.23% (w/w) of NaOH. The conductive medium had pH of about 4.5. The hydrophilic porous membrane 12, 13 was hydrophilic Durapore (trade name: manufactured by Nippon Millipore). The peeling liner 14, 15 attached to the hydrophilic porous membrane was a PET sheet. The adhesive tape 16 was Brenderm (manufactured by 3M).

An animal to be treated a drug was a 10-week old male SD rat (weight: about 400 g). The rat was anesthetized with pentobarbital. A part of the abdomen was shaved and an iontophoresis device was attached on the area. Paired two electrode terminals for the device were connected, as illustrated in FIG. 7, to the timer-equipped switch 3, the current generator 2 (50 kHz, 50% duty) and the power source 1. Then, switching iontophoresis administration was conducted for 24 hours under the condition of a constant transmitted current (current density: 0.075 mA/cm$^2$; total current: 0.72 mA). An area where current flows was the area where the hydrophilic porous membrane was in contact with the skin and whose area was 9.62 cm. The switching condition was repetition of polarity inversion in the electrode by 5 min where current flew to one direction for a time period defined by a timer and then polarity was instantaneously inverted by the action of a relay to restart energization. After initiation of administration, blood was sampled at regular intervals to determine a concentration of compound in serum by HPLC.

A serum sample was diluted with saline, applied to a pretreatment column (Bond Elut C18) to be absorbed by the column, eluted with 1% TFA-containing methanol solution to roughly removing serum components. After evaporation of the solvent under a nitrogen stream, the residue was dissolved in the HPLC eluent and then applied to HPLC. HPLC conditions were as follows:

HPLC conditions

Column: L-column (ODS; inner diameter: 4.6 mm; length: 150 mm; Kagakuhin Kensa Kyokai);

Eluent: 0.05 mol phosphate buffer (pH 3.5)/Acetonitrile/ 0.5 mol Sodium 1-octabesykfibate=85/15/1;

Flow rate: 1 ml/min;

UV wavelength: 254 nm.

Example 22

Figure 8:
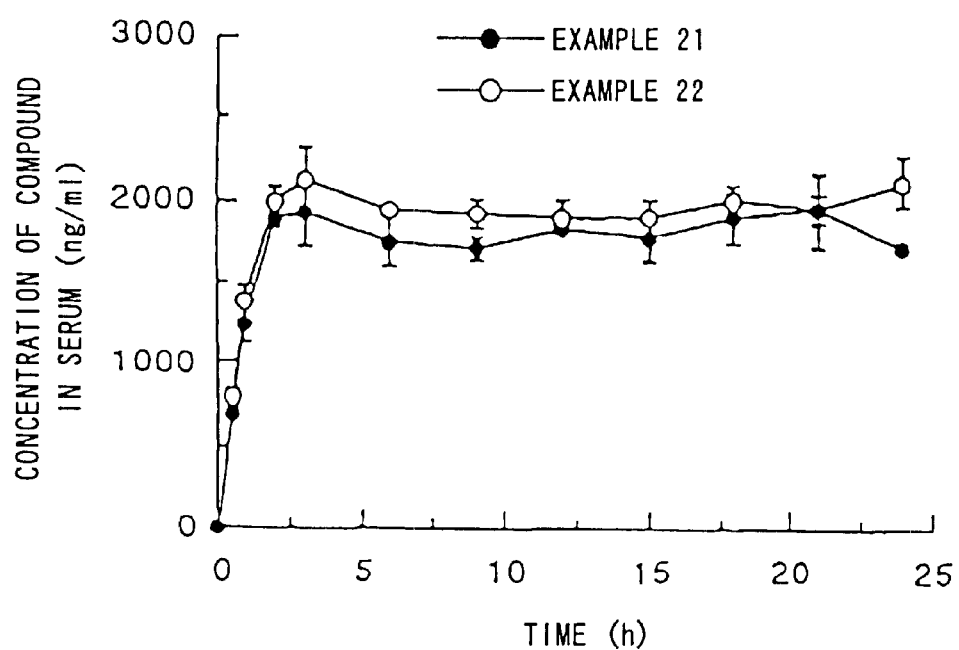
FIG. 8 is a graph illustrating variation with time of a concentration of compound in serum in Examples 21 and 22.

Concentrations of compound in serum were determined after iontophoresis administration to a rat using the same iontophoresis administration device as that in Example 21, under the conditions as described in Example 21 except that an inversion interval was 15 min. Variation of a concentration of compound in serum with the passage of time The variations of a blood compound level with the passage of time in Examples 21 and 22 are shown in FIG. 8. (In FIG. 8, black circles and white circles represent the results of Examples 21 and 22, respectively.) In both Examples, the concentration of compound in serum reached about 2000 ng/ml at 2 hours and the level was maintained to 24 hours. In other words, it was found that switching allowed electrificity to be maintained for a long period and higher transdermal absorptivity responding to energization to be maintained for a long period. As a control, energization was separately conducted in one direction without polarity inversion, using the iontophoresis delivery device of Example 21. As a result, a voltage was rapidly increased at about 1.5 hours, resulting in energization failure.

As another control, iontophoresis administration was separately conducted in one direction without polarity inversion using an electrode device unit having the same composition as that of Example 21 as a cathode electrode device unit except that the electrode was a silver foil and using a commercially available printed silver/silver chloride electrode as an anode electrode device unit, although the anode electrode unit was replaced by several hours; current density: 0.075 mA/cm$^2$). Comparing the concentration of compound in serum, the concentration in serum during steady state in Examples 21 and 22 exhibited skin-permeation promoting effect exceeding an expected level in 80% of the cases. It had been concerned that by polarity inversion, a compound which has been transferred to the skin side would be generally subject to reverse iontophoresis effect (a drug moves toward a cathode) so that expected skin-permeation promoting effect could not be achieved by iontophoresis. It can be concluded that the results of this example were obtained because of suitable selection of a compound, a polarity inverting time and a composition in the electrode device unit.

Example 23

An iontophoresis delivery device as illustrated in FIG. 7 was prepared, which contained the compound prepared in Preparation Example in conducting media 10, 11. The paired two electrode device units 4, 5 had the same disk figure where the inner diameter of the electrodes 8, 9 was 25 mm; the inner diameter and the volume of the conductive media 10, 11 were 30 mm and 1.3 ml, respectively; and the diameter of the hydrophilic porous membrane 12, 13 was 35 mm (corresponding to a surface area of 9.62 $cm^2$). The insulating support 6, 7 was a plastic (polyethylene terephthalate: PET) cup (an eaves length: about 5 mm). The electrode was that in which silver and silver chloride was printed on a sheet with a weight ratio of 1:1. The thickness of silver/silver chloride printed was about 15 $\mu$m. The conductive medium was a gel containing 4.32% (w/w) of the above compound, 1% (w/w) of agarose, 10% (w/w) of glycerol, 1.14% (w/w) of meglumine and 5% (w/w) of polysorbate 80. The conductive medium had pH of about 4.5. The hydrophilic porous membrane 12, 13 was hydrophilic Durapore (trade name: manufactured by Nippon Millipore). The peeling liner 14, 15 attached to the hydrophilic porous membrane was a PET sheet. The adhesive tape 16 was Brenderm (manufactured by 3M). Using the iontophoresis delivery device, the rat was subject to iontophoresis administration under the conditions described in Example 21 except that an inversion time interval was 30 min and a current density was 0.05 $mA/cm^2$, to determine a concentration of compound in serum. The results indicated that good absorption and an expectedly higher concentration of compound in serum were maintained for 24 hours (a concentration of compound in serum after 2 hours: about 2500 ng/ml). It was found that adding polysorbate 80 to the conductive medium contributed to reduce a power consumption (i.e., effect that a given current density can be obtained even after reducing an applied voltage to ½ or less).

Example 24

An iontophoresis delivery device as illustrated in FIG. 7 was prepared, which contained the compound prepared in Preparation Example in conducting media 10, 11. The paired two electrode device units 4, 5 had the same disk figure where the inner diameter of the electrodes 8, 9 was 25 mm; the inner diameter and the volume of the conductive media 10, 11 were 30 mm and 1.3 ml, respectively; and the diameter of the hydrophilic porous membrane 12, 13 was 35 mm (corresponding to a surface area of 9.62 $cm^2$). The insulating support 6, 7 was a plastic (polyethylene terephthalate: PET) cup (an eaves length: about 5 mm). The electrode was that in which silver and silver chloride was printed on a sheet with a weight ratio of 1:1. The thickness of silver/silver chloride printed was about 15 $\mu$m. The conductive medium was a gel containing 4.32% (w/w) of the above compound, 1% (w/w) of agar, 10% (w/w) of glycerol, 1.14% (w/w) of meglumine, 0.1% (w/w) of polysorbate 80, 0.2% (w/w) of methylparaben and 0.2% (w/w) of benzoic acid. The conductive medium had pH of about 4. The hydrophilic porous membrane 12, 13 was hydrophilic Durapore (trade name: manufactured by Nippon Millipore). The peeling liner 14, 15 attached to the hydrophilic porous membrane was a PET sheet. The adhesive tape 16 was Brenderm (manufactured by 3M). Using the iontophoresis delivery device, the rat was subject to iontophoresis administration under the conditions described in Example 21 except that an inversion time interval was 10 min and a current density was 0.05 $mA/cm^2$, to determine a concentration of compound in serum. The results indicated that good absorption and an expectedly higher concentration of compound in serum were maintained for 24 hours (a concentration of compound in serum after 2 hours: about 2000 ng/ml). As was in Example 23, it was found that adding polysorbate 80 to the conductive medium contributed to reduce a power consumption (i.e., effect that a given current density can be obtained even after reducing an applied voltage to ½ or less).

Example 25

A rat was subject to iontophoresis administration using the iontophoresis device described in Example 24, under the conditions described in Example 24 except that a current density was 0.1 $mA/cm^2$ from the initiation of administration to 120 min and thereafter was 0.05 mA/cm , to determine a concentration of compound in serum. The concentration of compound in serum in the rat was determined.

The results showed that relatively faster transdermal absorption occurred from the initiation of administration to 120 min and a time taken for making a concentration of compound in serum steady was thus reduced.

Example 26

An iontophoresis delivery device was prepared as described in Example 24, except that in terms of the paired two electrode device units 4 and 5, the conductive medium in one electrode device unit 5 was replaced with a medium made of a gel without the above compound or methylglucamine while the above compound was added to the other electrode device unit 4. Using the delivery device, a rat was subject to iontophoresis administration as described in Example 21, except that the inversion condition was a sequence of 30 min energization, 30 min non- energization, polarity inversion and then restarting energization, a current density 0.05 $mA/cm^2$, and at the beginning of administration, the electrode device unit 4 was an anode, to determine a concentration of compound in serum.

As a result, a concentration of compound in serum was increased because of transdermal absorption of the compound 30 min after administration. During subsequent 90 min, a concentration of compound in serum was reduced due to stop of transdermal absorption. After the electrode device unit 4 again became an anode, transdermal absorption was restarted to increase a concentration in serum substantially to the original level. The pattern was repeated. In other words, it can be concluded that when the electrode device unit 4 containing the compound became an anode, transdermal absorption occurred to increase a concentration in serum while transdermal absorption was stopped during the other period to reduce a concentration in serum, and such stable pulse-type concentration of compound in serum variation was repeated for 24 hours.

Example 27

A rat was subject to iontophoresis administration as described in Example 26, except that the inversion condition was a sequence of 30 min energization, 10 min non-energization, polarity inversion and then restarting energization, to determine a concentration of compound in serum.

As a result, a concentration of compound in serum was reduced because of transdermal absorption of the compound 30 min after administration. After the electrode device unit 4 again became an anode, transdermal absorption occurred. The pattern was repeated. In other words, it can be concluded that when the electrode device unit 4 containing the compound became an anode, transdermal absorption occurred to increase a concentration in serum while transdermal absorption was stopped during the other period to reduce a concentration in serum, and a pulse peak in such pulse-type concentration of compound in serum variation tended to be slightly increased as inversion was repeated.

Example 28

An iontophoresis delivery device is prepared as described in Example 24, except that in terms of the paired two electrode device units 4 and 5, the conductive medium in one electrode device unit 5 is replaced with a medium consisting of a gel containing the ¼ amounts of the above compound and of methylglucamine, to provide an iontophoresis delivery device in which a compound concentration is different between these electrode device units.

Using the delivery device, a rat is subject to iontophoresis administration as described in Example 21, except that the inversion condition is a sequence of 30 min energization, 10 min non-energization, polarity inversion and then restarting energization; a current density is 0.05 mA/cm$^2$; and the electrode device unit 4 is an anode at the initiation of administration, to determine a concentration of compound in serum.

As a result, a concentration of compound in serum is increased because of transdermal absorption of the compound 30 min after administration. During 50 min until the electrode device unit 4 becomes an anode, increase of a concentration of compound in serum becomes slower due to stop of transdermal absorption or reduction in a transdermal absorption rate. After the electrode device unit 4 again becomes an anode, transdermal absorption is further increased to reach the original level. The pattern is repeated. In other words, during 24 hours, the overall administration period, a concentration of compound in serum is maintained within a substantially certain range.

INDUSTRIAL APPLICABILITY

As described above, the present invention provides a long-term type iontophoresis device with higher versatility and practicability for achieving improved drug bioavailability which may be applied to a variety of drugs and whereby effective and continuous absorption may be maintained for a long period during which energization and absorbability can be maintained without reducing a drug delivery rate. Specifically, safe, effective and continuous absorption can be maintained for a long period by using an active electrode made of a mixture comprising silver and silver chloride, two electrode structures containing a given amount of chloride ions and an active ingredient, and a power supply equipped with polarity inverting means. In the device of the present invention, the amount of chloride ions and the polarity inverting time may be optimized to transdermally deliver a drug with higher bioavailability and good reproducibility without being influenced by the polarity of the drug.

What is claimed is:

1. An iontophoresis device comprising: first and second electrode structures each having a hydrophilic conductive layer containing at least one active ingredient and an electrode member made of an active electrode material; and a power supply having polarity inverting means which is electrically connected between the electrode members in the first and the second electrode structures for switching over a current direction between the two electrode structures, wherein at least one of the first and the second electrode structures contains chloride ions and before administration, a chloride-ion content (P mg) is within a range satisfying the following equation:

$$1.0 \times (I \times T \times 0.022) \leq P$$

wherein T represents a polarity inverting time (min) until polarity is inverted after energization in a certain direction and I represents an average current (mA).

2. The iontophoresis device according to claim 1, wherein the electrode member is formed by printing a conductive ink containing at least silver and silver chloride.

3. The iontophoresis device according to claim 2, wherein a composition ratio or mixing ratio of silver and silver chloride in the electrode member is 1:9 to 9:1.

4. The iontophoresis device according to claim 2, wherein the electrode member further contains a halogenated compound.

5. The iontophoresis device according to claim 1, wherein the chloride ions are supplied from a resin or polymer containing at least quaternary ammonium chloride.

6. The iontophoresis device according to claim 5, wherein the resin is selected from the group consisting of ethyl acrylate-methyl methacrylate-methyl methacrylate trimethylammonium chloride copolymers and cholestyramine.

7. The iontophoresis device according to claim 1, wherein the electrode structure contains an organic amine as a pH adjusting material.

8. The iontophoresis device according to claim 7, wherein the pH adjusting material is at least one of meglumine, tromethamol, triethanolamine and aminoacrylate.

9. The iontophoresis device according to claim 1, wherein the active ingredient is neutral or cationic and polarity inversion is periodically repeated by the power supply.

10. The iontophoresis device according to claim 1 wherein the power supply includes timer means for controlling a polarity inverting time.

11. The iontophoresis device according to claim 1, wherein chloride ions are contained in the hydrophilic conductive layer or an additional hydrophilic conductive layer placed between the electrode member and the hydrophilic conductive layer.

12. The iontophoresis device according to claim 1, wherein first and second electrode structures have the same composition containing a given amount of chloride ions at least one active ingredient.

13. The iontophoresis device according to claim 1, wherein the chloride ions are supplied from hydrochloric acid.

14. The iontophoresis device according to claim 1, wherein the chloride ions are supplied from at least one active ingredient hydrochloride.

15. The iontophoresis device according to claim 1, wherein the power supply includes means for shorting a circuit in polarity inversion and/or means for providing a non-energization time for a given period.

16. The iontophoresis device according to claim 1, wherein the polarity inversion by the power supply is conducted at least once and a time for one polarity inversion is 1 min to 2 hours.

17. The iontophoresis device according to claim 1, wherein the current applied by the power supply is at least one of direct current, pulse direct current and pulse depolarized direct current.

18. The iontophoresis device according to claim 1, wherein the electrode structures include an insulating support having a pit, which accommodates the electrode member and the hydrophilic conductive layer therein and whose surface is covered by a semipermeable membrane, a selective permeation membrane, a control membrane or a hydrophilic porous membrane.

19. An iontophoresis device comprising: first and second electrode structures each having a hydrophilic conductive layer containing at least one active ingredient and an electrode member made of an active electrode material; and a power supply having polarity inverting means which is electrically connected between the electrode members in the first and the second electrode structures for switching over a current direction between the two electrode structures, wherein at least one of the first and the second electrode structures contains chloride ions and before administration, a chloride-ion content (P mg) is within a range satisfying the following equation:

$$1.0 \times (I \times T \times 0.022) \leq P \leq 100 \times (I \times T \times 0.022)$$

wherein T represents a polarity inverting time (min) until polarity is inverted after energization in a certain direction and I represents an average current (mA).

20. The iontophoresis device according to claim 19, wherein the active ingredient is anionic and polarity inversion is periodically repeated by the power supply.

* * * * *